United States Patent [19]

Hamanaka et al.

[11] Patent Number: 5,536,736
[45] Date of Patent: Jul. 16, 1996

[54] TRIAZOLYL-PHENOXYACETIC ACID COMPOUNDS WHICH HAVE USEFUL PHARMACEUTICAL UTILITY

[75] Inventors: Nobuyuki Hamanaka; Kanji Takahashi; Hidekado Tokumoto, all of Osaka, Japan

[73] Assignee: Ono Pharmaceutical Co., Ltd., Osaka, Japan

[21] Appl. No.: 293,218

[22] Filed: Aug. 19, 1994

Related U.S. Application Data

[62] Division of Ser. No. 24,306, Mar. 1, 1993, Pat. No. 5,378,716.

[30] Foreign Application Priority Data

Feb. 28, 1992  [JP]  Japan ................... 4-078330

[51] Int. Cl.[6] ................. C07D 249/04; A61K 31/41
[52] U.S. Cl. ........................... 514/359; 548/255
[58] Field of Search .................... 548/255; 514/359

[56] References Cited

PUBLICATIONS

Biagi et al, IL. Farmaco, vol. 43 (7–8) 1988, pp. 597–611.
Biagi et al, IL Farmaco, vol. 41(8), 1986, pp. 597–610.
Chemical Abstracts, vol. 114, Abstract No. 185, 397y, 1991, p.781.

*Primary Examiner*—Zinna Northington Davis
*Attorney, Agent, or Firm*—Sughrue, Mion, Zinn, Macpeak & Seas

[57] ABSTRACT

We proposed a novel compound having an activity of $PGI_2$ receptor agonist.

A phenoxyacetic acid derivative of the formula

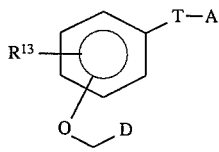

A is $-C(R^1)=N-OR^2$, $-CH(R)NH-OR^2$, $-COE$, $-SO_2E$, $-CH_2-NR^3-Y$, $-Z-NR^3-CONR^4R^5$, $-CH_2-OR^6$, $-CO_2R^6$, $-CH_2-O-N=CR^7R^8$, $-CH_2-O-NHCHR^7R^8$, substituted by imidazolyl(methyl), pyrazolylmethyl, oxazolyl(methyl), thioxazolyl, isoxazolyl, isothiazolyl, oxadiazolyl, triazolylmethyl;

T is alkylene, alkenylene, etc.;

D is $-CO_2R^{10}$, $-CONR^{11}R^{12}$;

E is (substitution) amino, hydradino;

Y is substituted (thio) carbonyl, substituted sulfonyl;

Z is $-CH=N-$, $-CH_2NR^3-$;

$R^1$, $R^3$, $R-R^{13}$ is each H or alkyl, etc.;

$R^2$, $R^4-R^9$ is each H, alkyl or alkyl substituted by phenyl or hetero ring, etc. and non-toxic salts thereof, non-toxic acid addition salts thereof, possess an agonistic on $PGI_2$ receptor, so it is useful for prevention and/or treatment of thrombosis, arteriosclosis, ischemic heart diseases, gastric ulcer and hypertention.

9 Claims, No Drawings

TRIAZOLYL-PHENOXYACETIC ACID COMPOUNDS WHICH HAVE USEFUL PHARMACEUTICAL UTILITY

This is a Divisional of application Ser. No. 08/024,306 filed on Mar. 1, 1993 now U.S. Pat. No. 5,378,716.

SUMMARY

This invention is related to phenoxyacetic acid derivatives.

More particularly, this invention is related to:

1) phenoxyacetic acid derivatives of the formula (I):

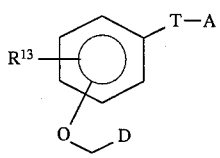

wherein all the symbols are the same meaning as hereafter defined, and non-toxic salts thereof and non-toxic acid addition salts thereof, 2) processes for the preparation thereof, and 3) pharmaceutical agents containing them as active ingredient.

BACKGROUND OF THE INVENTION

Prostaglandin $I_2$ ($PGI_2$) is a physiologically active natural substance having the following structural formula, which is biosynthesized from Prostaglandin $H_2$ ($PGH_2$) in the metabolic process the called arachidonate cascade.

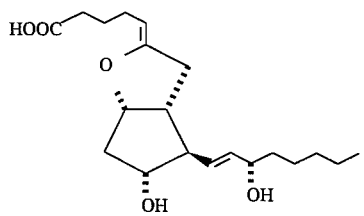

(see Nature, 263, 663(1976), Prostaglandins, 12, 685(1976), ibid, 12, 915(1976), ibid, 13, 375(1977) and Chemical and Engineering News, Dec. 20, 17(1976)).

$PGI_2$ has been confirmed to possess not only a very strong inhibitory activity on blood platelet aggregation but a dissociative activity on blood platelet aggregation, an inhibitory activity on blood platelet adhesion, a vasodilating activity, an inhibitory activity on gastric acid secretion etc. Therefore, it has been considered that $PGI_2$ is useful for the prevention and/or the treatment for thrombosis, arteriosclerosis, ischemic heart diseases, gastric ulcer, hypertension etc. But its application as a pharmaceutical is limited because of its chemical instability the difficulty in separating the activities according to purpose. Accordingly, various $PGI_2$ derivatives have been synthesized and much research has been carried out for the maintenance and the separation of the activities. However, no satisfactory results have been obtained.

Recently, to solve two problems described above research for $PGI_2$ receptor agonists which have a new skeleton which may be useful for the treatment of or for the prevention of the above diseases, in view of $PGI_2$ receptor level, has been carried out.

RELATED ARTS

It has been reported in the literature, that the following compounds not having the $PGI_2$ skeleton are $PGI_2$ receptor agonists which bind to a $PGI_2$ receptor and inhibit blood platelet aggregation:

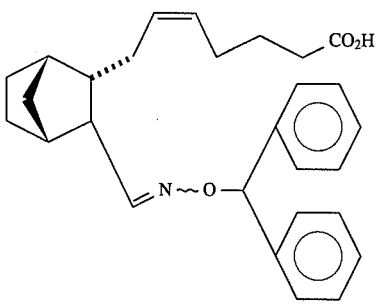

(see Brit. J. Pharmacot., 76, 423(1982), ibid, 84, 595(1985), and the Japanese Patent Kohyo No. 55-501098),

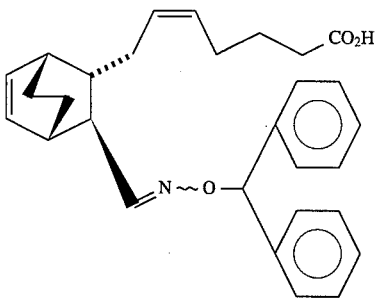

(see Brit. J. Pharmacol., 76, 423(1982), ibid, 84, 595(1985), and the Japanese Patent Kohyo No. 57-501127),

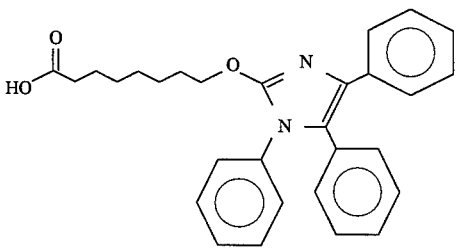

(see Brit. J. Pharmacol., 102, 251–266(1991) and the West German Patent Publication No. 3,504,677), and

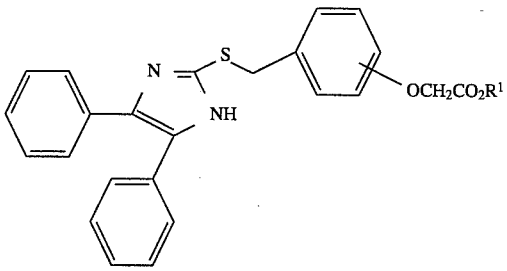

(see U.S. Pat. No. 5,011,851).

PURPOSE OF THE INVENTION

Energetic investigation has been carried out to discover new $PGI_2$ receptor agonists having a skeleton with a chemical structure different from the compounds mentioned above present inventors have found that phenoxyacetic acid derivatives can bind to $PGI_2$ receptor and have an inhibitory activity on blood platelet aggregation.

The phenoxyacetic acid derivatives of formula (I) of the instant invention are novel, and it is not possible to predict from the above compounds known as $PGI_2$ receptor agonists, that the compounds of the instant invention are $PGI_2$ receptor agonists.

DETAILED DISCLOSURE OF THE INVENTION

The present invention is related to:

1) Phenoxyacetic acid derivatives of the formula (I):

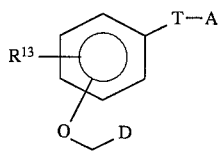
(I)

wherein A is i) $-CR^1=N-OR^2$,
ii) $-CHR^1-NH-OR^2$,
iii) $-COE$,
iv) $-SO_2E$,
v) $-CH_2-NR^3-Y$,
vi) $-Z-NR^3-CONR^4R^5$,
vii) $-CH_2-OR^6$,
viii) $-CO_2R^6$,
ix) $-CH_2-O-N=CR^7R^8$,
x) $-CH_2-O-NHCHR^7R^8$,

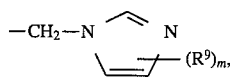 xi)

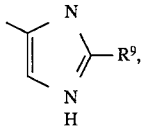 xii)

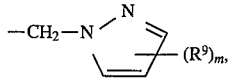 xiii)

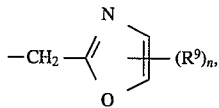 xiv)

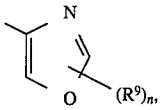 xv)

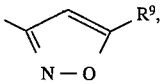 xvi)

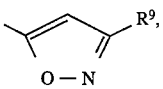 xvii)

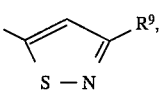 xviii)

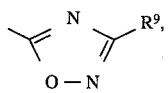 xix)

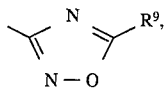 xx)

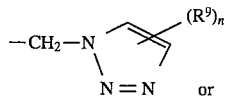 xxi)

or

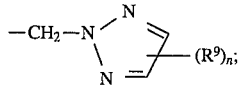 xxii)

T is i) single bond, ii) C1–6 alkylene, iii) C2–6 alkenylene or iv) $-O-(CH_2)_s-$;

D is i) $-CO_2R^{10}$ or ii) $-CONR^{11}R^{12}$;

E is i) $-NR^4R^5$, ii) $-NR^3OR^6$, iii) $-NR^3-NR^4R^5$ or iv) $-NR^3-N=CR^4R^5$;

Y is i) $-COR^6$, ii) $-CO-L-NR^4R^5$, iii) $-CS-NHR^4$ or iv) $-SO_2R^6$;

Z is i) $-CH=N-$ or ii) $-CH_2-NR^3-$;

L is single bond or C1–4 alkylene;

$R^1$ is hydrogen, C1-6 alkyl or phenyl;

$R^2$ is i) C1–8 alkyl substituted by one or two of phenyl, 4–7 membered monocyclic hetero ring containing one nitrogen or C4–7 cycloalkyl, ii) C10–15 hydrocarbon condensed tricyclic ring or iii) C1–15 alkyl;

$R^3$ is hydrogen, C1-6 alkyl or phenyl;

$R^4$ and $R^5$ each, independently, is i) hydrogen, ii) phenyl, iii) 4–7 membered monocyclic hetero ring containing one nitrogen or iv) C1–4 alkyl substituted by one or two of phenyl or 4–7 membered monocyclic hetero ring containing one nitrogen;

$R^6$ is i) phenyl, ii) 4–7 membered monocyclic hetero ring containing one nitrogen or iii) C1–4 alkyl substituted by one to three of phenyl or 4–7 membered monocyclic hetero ting containing one nitrogen;

$R^7$ is i) hydrogen, ii) C 1–8 alkyl, iii) phenyl or C4–7 cycloalkyl, iv) 4–7 membered monocyclic hetero ring containing one nitrogen or v) C1–4 alkyl substituted by one or two of phenyl, C4–7 cycloalkyl or 4–7 membered monocyclic hetero ring containing one nitrogen;

$R^8$ is i) C1–8 alkyl, ii) phenyl or C4–7 cycloalkyl iii) 4–7 membered monocyclic hetero ring containing one nitrogen or iv) C1–4 alkyl substituted by one or two of phenyl, C4–7 cycloalkyl or 4–7 membered monocyclic hetero ring containing one nitrogen;

$R^9$ is i) hydrogen, ii) phenyl, iii) C1–4 alkyl or iv) C1–4 alkyl substituted by one or two of phenyl or 4–7 membered monocyclic hetero ring containing one nitrogen;

$R^{10}$ is hydrogen or C1–12 alkyl;

$R^{11}$ and $R^{12}$ each, independently, is hydrogen or C1–4 alkyl or $R^{11}$ and $R^{12}$, taken together with nitrogen bond to $R^{11}$ and $R^{12}$ is the reside of an amino acid;

$R^{13}$ is hydrogen, C1–4 alkyl, C1–4 alkoxy or nitro;

m is 1–3, n is 1–2, s is 2–4;

and the rings of $R^1$, $R^2$, $R^3$, $R^4$, $R^5$, $R^6$, $R^7$, $R^8$ and $R^9$ also may be substituted by one to three of C1–C4 alkyl, C1–C4 alkoxy, halogen, nitro or trihalomethyl;

with the proviso that, (1) when A is —$SO_2E$ wherein E is the same meaning hereinbefore defined, T is not single bond and C1 alkylene (methylene), (2) when A is

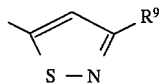

where in $R^9$ is the same meaning hereinbefore defined, T is not C2–6 alkenylene; and non-toxic salts thereof and non-toxic acid addition salts thereof.

2) Process for the preparation of them and

3) Pharmaceutical agent containing them as active ingredient.

Unless specified, all isomers are included in the invention. For example, alkyl, alkoxy, alkylene and alkenylene includes straight and branched ones. Double bond in alkenylene and oxime include E, Z the and EZ mixture. Isomers generated by asymmetric carbon(s) e.g. branched alkyl are included in the instant invention.

The compounds of formula (I) of the instant invention, wherein $R^{10}$ is hydrogen, may be convened into the corresponding salts by methods known per se. Non-toxic and water-soluble salts are preferable. Suitable salts, for example, am salts of alkaline metals (potassium, sodium, etc.), salts of alkaline earth metals (calcium, magnesium, etc.), ammonium salts, salts of pharmaceutically-acceptable organic amines (tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucamine, etc,).

The compounds of formula (I) may be converted into the corresponding acid additional salts by methods known per se. Non-toxic and water-soluble salts are preferable. Suitable acid addition salts, for example, are salts of inorganic acids, e.g., hydrochloride, hydrobromide, sulphate, phosphate, nitrate etc., or salts of organic acids, e.g., acetate, lactate, tartarate, oxalate, fumarate, maleate, citrate, benzoate, methanesulphonate, ethanesulphonate, benzenesulphonate, toluenesulphonate, isethioate, glucuronate, gluconate etc.

The compounds of formula (I), salts thereof or acid additional salts thereof may be converted into hydrates thereof by methods known per se.

In formula (I), C1–4 alkylene represented by L means methylene ethylene, trimethylene, tetramethylene and isomeric groups thereof. C1–6 alkylene represented by T means methylene, ethylene, trimethylene. tetramethylene, pentamethylene, hexamethylene and isomeric groups thereof. C2–6 alkenylene represented by T means ethylene, trimethylene tetramethylene, pentamethylene, hexamethylene and isomeric groups thereof having one or two double bond.

In formula (I), C1–4 alkyl represented by $R^4$, $R^5$, $R^6$, $R^7$, $R^8$, $R^9$, $R^{11}$, $R^{12}$ and $R^{13}$ means methyl, ethyl, propyl, butyl and isomeric groups thereof. C1–6 alkyl represented by $R^1$ and $R^3$ means methyl, ethyl, propyl, butyl, pentyl, hexyl and isomeric groups thereof. C1–8 alkyl represented by $R^2$, $R^7$ and $R^8$ means methyl, ethyl, propyl, butyl, pentyl, hexyl, heptyl, octyl and isomeric groups thereof. C1–15 alkyl represented by $R^2$ means methyl, ethyl, propyl, butyl, pentyl, hexyl, heptyl, octyl, nonyl, decyl, undecyl, dodecyl, tridecyl, tetradecyl, pentadecyl and isomeric groups thereof. C1–12 alkyl represented by $R^{10}$ means methyl, ethyl, propyl, butyl, pentyl, hexyl, heptyl, octyl, nonyl, decyl, undecyl, dodecyl and isomeric groups thereof.

In formula (I), C1–4 alkoxy represented by $R^{13}$ means methoxy, ethoxy, propoxy, butoxy and isomeric groups thereof.

In formula (I), C4–7 cycloalkyl represented by $R^2$, $R^7$ and $R^8$ means for example, cyclopentyl, cyclohexyl and cycloheptyl.

In formula (I), 4–7 membered monocyclic hetero ring represented by $R^2$, $R^4$, $R^5$, $R^6$, $R^7$, $R^8$ and $R^9$ means for example, pyrrole, pyridine, azepine ring and partially or fully saturated ring thereof (e.g., pyrrolidine, piperidine ring, etc.).

In the formula (I), C10–15 hydrocarbon condensed tricyclic ring means, for example, indacene, fluorene, anthracene, dibenzocycloheptene rings and partially or fully saturated ring thereof.

In formula (I), C1–C4 alkyl as substituents of the rings in $R^1$, $R^2$, $R^3$, $R^4$, $R^5$, $R^6$, $R^7$, $R^8$ and $R^9$ mean methyl, ethyl, propyl, butyl and isomers thereof. C1–C4 alkoxy means methoxy, ethoxy, propoxy, butoxy and isomers thereof. Halogen and halogen in trihalomethyl means fluorine, chlorine, bromine and iodine atoms.

Examples of representative compounds of formula (I), of the instant invention are:

(1) 3-[2-[2-Phenyl-2-(3-pyridyl)ethyl]oxyiminoethyl]phenoxyacetic acid, (2) 3-[2-(2-Cyclohexyl-2-phenylethyl)oxyiminoethyl]phenoxyacetic acid, (3) 3-[2-[2-(Fluorene-9-yl)ethyl]oxyiminoethyl]phenoxyacetic acid, (4) 3-[2-(2-Phenyldecyl)oxyiminoethyl]phenoxyacetic acid, (5) 4-(2-Benzoylaminoethyl)phenoxyacetic acid, (6) 4-[2-(N,N-Diphenylaminocarbonylamino )ethyl]phenoxyacetic acid, (7) 4-[2-(N,N-Diphenylaminomethylcarbonylamino)ethyl]phenoxyacetic acid, (8) 4-(2-Phenylaminothiocarbonylaminoethyl)phenoxyacetic acid, (9) 4-(2-Phenylsulfonylaminoethyl)phenoxyacetic acid,

(10) 4-[2-(N,N-Diphenylaminocarbonylaminoimino)ethyl] phenoxyacetic acid,

(11) 3-[3-(2-Diphenylmethylimidazol-5-yl)propyl]phenoxyacetic acid,

(12) 3-[3-(3,4,5-Triphenylpyrazol-1-yl)propyl]phenylacetic acid,

(13) 3-[3-(Oxazol-2-yl)propyl]phenoxyacetic acid,

(14) 3-[3-(5-Ethyloxazol-4-yl)propyl]phenoxyacetic acid,

(15) 3-[3-[5-Di(3-pyridly)methylisoxazol-3-yl]propyl]phenoxyacetic acid,

(16) 3-[3-(4,5-Diphenylimidazolyl)propyl]phenoxyacetic acid,

(17) 3-[3-(5-Diphenylmethylisoxazol-3-yl)propyl]phenoxyacetamide,

(18) Amide of 3-[3-(5-Diphenylmethylisoxazol-3-yl)propyl] phenoxyacetic acid with glycine,

(19) Octyl 3-[3-(5-diphenylmethylisoxazol-3-yl)propyl] phenoxyacetate,

(20) 3-[3-[4-Di(3-pyridyl)methylpyrazol-1-yl]propyl]phenoxyacetic acid,

(21) 2-Methyl-3-[3-[4-[1-phenyl-1-(3-pyridyl)methyl]pyrazol- 1-yl]propyl]phenoxyacetic acid,

(22) 3-[3-Di(3-pyridyl)methyloxyiminopropyl]phenoxyacetic acid,

(23) 3-[3-[Di(3-pyridyl)methylideneaminooxy]propyl]phenoxyacetic acid,

(24) 3-[3-[1-cyclohexyl-1-Phenylmethylideneaminooxy]propyl]phenoxyacetic acid,
(25) 2-Methyl-3-[3-[1-phenyl-1-(3-pyridyl)methylideneaminooxy]propyl]phenoxyacetic acid,
(26) 3-(3-Diphenylmethyloxyaminosulfonylpropyl)phenoxyacetic acid,
(27) 3-[3-[(N,N-Diphenylamino)aminosulfonyl]propyl]phenoxyacetic acid,
(28) 3-[3-[(1,1-Diphenylmethylideneamino)aminosulfonyl)propyl]phenoxy acetic acid,
(29) 4-[2-[(N,N-Diphenylaminocarbonylamino)amino]ethyl]phenoxyacetic acid,
(30) 3-[3-[5-[1-Phenyl-1-(3-pyridyl)methyl]isoxazol-3-yl]propyl]phenoxyacetic acid,
(31) 3-[4-Methyl-4-(1-phenyl-1-(3-pyridyl)methyloxyimino)butyl]phenoxyacetic acid,
(32) 3-[2-[4-[1-Phenyl-1-(3-pyridyl)methyl]pyrazol-1-yl]ethyl]phenoxyacetic acid,
(33) 3-[3-[1-Phenyl-1-(3-pyridyl)methylaminooxy]propyl]phenoxyacetic acid, non-toxic salts thereof and non-toxic acid addition salts thereof those described in the examples below.

PROCESS FOR THE PREPARATION

The compounds of the instant invention of formula (I), may be prepared:

(i) by reacting a compound of formula (III):

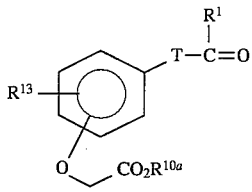

(III)

wherein $R^{10a}$ means methyl or ethyl and the other symbols have the same meaning as hereinbefore defined, with a compound of formula (a):

$R^2ONH_2$       (a)

wherein $R^2$ has the same meaning as hereinbefore defined, (ii) by subjecting a compound obtained by reaction (i) of formula (Ia-1):

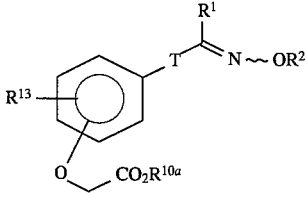

(Ia-1)

wherein all the symbols have the same meaning as hereinbefore defined, to reduction, (iii) by amidation of a compound of formula (IV):

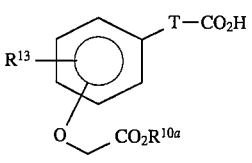

(IV)

wherein all the symbols have the same meaning as hereinbefore defined, with a compound of formula (b):

H E       (b)

wherein E has the same meaning as hereinbefore defined, (iv) by subjecting a compound of formula (VI):

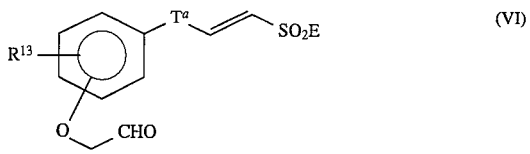

(VI)

wherein $T^a$ is single bond, C1–4 alkylene C2–4 alkenylene, or $-O-(CH_2)_t-$ wherein t is 0–2, and the other symbols have the same meaning as hereinbefore defined, to Jone's oxidation, (v) by subjecting a compound obtained by reaction (iv) of formula (Ib-1):

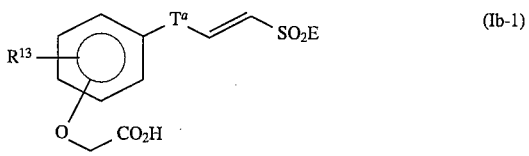

(Ib-1)

wherein all the symbols have the same meaning as hereinbefore defined, to hydrogenation (including a series of reactions subjecting a compound of formula (Ib-1) to methylesterification and to hydrogenation, followed by hydrolysis of the ester bond, for the convenience of purification), (vi) by amidation or thioamidation of a compound of formula (VIII):

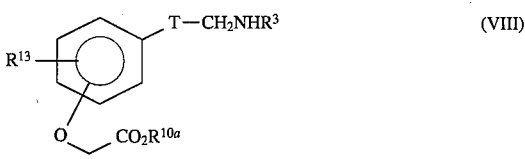

(VIII)

wherein all the symbols have the same meaning as hereinbefore defined, with a compound of formula (c):

$R^6CO_2H$       (c)

wherein $R^6$ have the same meaning as hereinbefore defined, or with a compound of formula (d):

$R^4R^5N-L-CO_2H$       (d)

wherein all the symbols have the same meaning as herein before defined, or with a compound of formula (e):

$R^4-N=C=S$       (e)

wherein $R^4$ has the same meaning as hereinbefore defined, or with a compound of formula (f):

$R^6SO_2Cl$       (f)

wherein $R^6$ is the same meaning as hereinbefore defined, (vii) by reacting a compound of formula (VII):

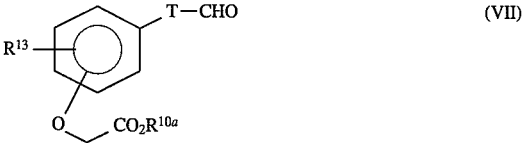

(VII)

wherein all the symbols have the same meaning as hereinbefore defined, with a compound of formula (g):

$H_2N-NR^3-CONR^4R^5$       (g)

wherein all the symbols have the same meaning as hereinbefore defined, (viii) by subjecting a compound obtained by reaction (vii) of formula (Ia-5):

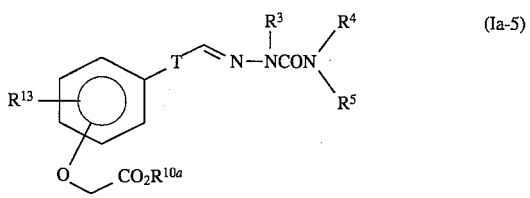

wherein all the symbols have the same meaning as hereinbefore defined, to reduction, (ix) by reacting a compound obtained by reaction (viii) of the formula (Ia-6):

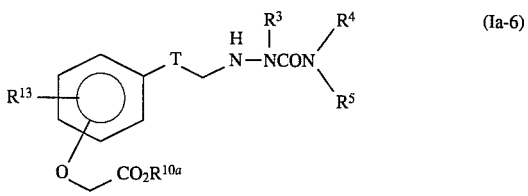

wherein all the symbols have the same meaning as hereinbefore defined, with a compound of formula (h):

R$^{3a}$I         (h)

wherein R$^{3a}$ is C1–6 alkyl or phenyl, (x) by reacting a compound of formula (II):

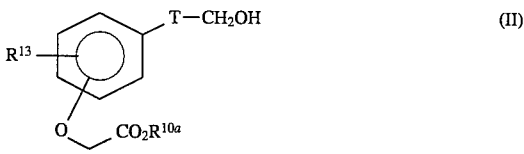

wherein all the symbols have the same meaning as hereinbefore defined, with a compound of formula (i):

wherein R$^6$ has the same meaning as hereinbefore defined, or with a compound of the formula (s):

R$^6$X         (s)

wherein X has halogen and R$^6$ is the same meaning as hereinbefore defined, (xi) by esterification of a compound of formula (IV):

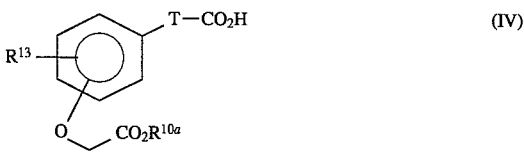

wherein all the symbols have the same meaning as hereinbefore defined, with a compound of formula (j):

R$^6$OH         (j)

wherein R$^6$ has the same meaning as hereinbefore defined, (xii) by reacting a compound of formula (IX):

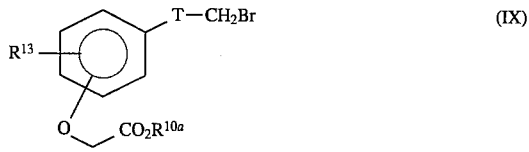

wherein all the symbols have the same meaning as hereinbefore defined, with a compound of formula (k):

G H         (k)

wherein G is

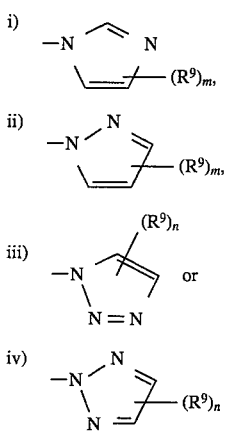

wherein all the symbols have the same meaning as hereinbefore defined, or with a compound of formula (q):

HO—N=CR$^7$R$^8$         (q)

wherein all the symbols have the same meaning a hereinbefore defined, or with a compound of formula (r):

HO—NH—CHR$^7$R$^8$         (r)

wherein all the symbols have the same meaning as hereinbefore defined, (xiii) by reacting a compound of formula (x):

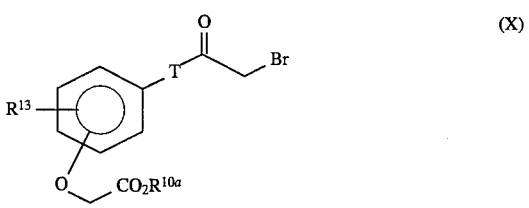

wherein all the symbols have the same meaning as hereinbefore defined, with a compound of formula (I):

wherein R$^9$ has the same meaning as hereinbefore defined, (xiv) by reacting a compound of formula (XII):

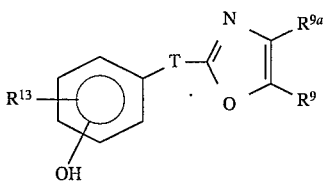

wherein $R^{9a}$ is phenyl, C1–4 alkyl or C1–4 alkyl substituted by one or two of phenyl or 4–7 membered monocyclic hetero ring containing one nitrogen and the other symbols have the same meaning as hereinbefore defined, or a compound of formula (XIV):

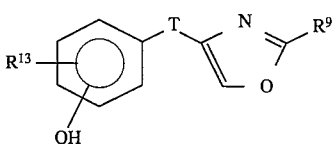

wherein all the symbols have the same meaning as hereinbefore defined, or a compound of formula (XVII):

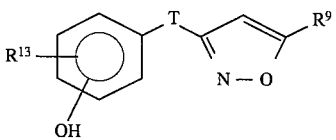

wherein all the symbols have the same meaning as hereinbefore defined, or a compound of formula (XXIII):

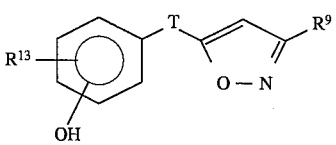

wherein all the symbols the the same meaning as hereinbefore defined, or a compound of formula (XXIX):

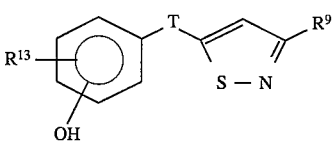

wherein all the symbols have the same meaning as hereinbefore defined, with a compound of formula (m):

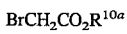 (m)

wherein $R^{10a}$ has the same meaning as hereinbefore defined,
(xv) by reacting a compound of the formula (XV):

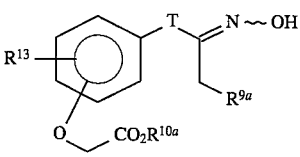

wherein all the symbols have the same meaning as hereinbefore defined, with a compound of formula (n):

 (n)

wherein $R^9$ has the same meaning as hereinbefore defined, (xvi) by cyclization of a compound of formula (XVIII):

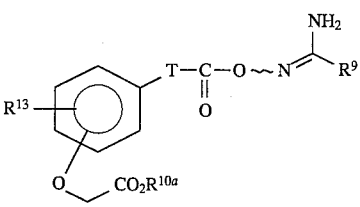

wherein all the symbols have the same meaning as hereinbefore defined, (xvii) by cyclization of a compound of formula (XX):

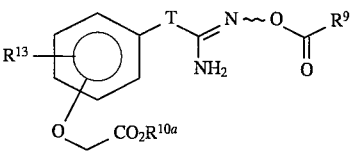

wherein all the symbols have the same meaning as hereinbefore defined, (xviii) by hydrolysis of a compound obtained by hereinbefore reaction (i), (ii), (iii), (vi), (vii), (viii), (ix), (x), (xi), (xii), (xiii), (xiv), (xv), (xvi) or (xvii) of formula (Ia):

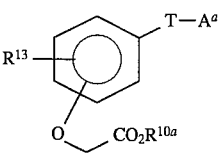

wherein $A^a$ is
  i) —CR$^1$=N—OR$^2$,
  ii) —CHR$^1$—NH—OR$^2$,
  iii) —COE,
  iv) —CH$_2$NR$^3$—Y,
  v) —CH=N—NR$^3$—CONR$^4$R$^5$,
  vi) —CH$_2$—NH—NR$^3$—CONR$^4$R$^5$,
  vii) —CH$_2$—NR$^{3a}$—NR$^3$—CONR$^4$R$^5$,
  viii) —CH$_2$OR$^6$,
  ix) —CO$_2$R$^6$,
  x) —CH$_2$G,
  xi) —CH$_2$—O—N=CR$^7$R$^8$,
  xii) —CH$_2$—O—NHCHR$^7$R$^8$, xiii) 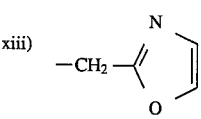

xiv) 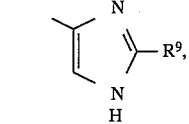

xv) 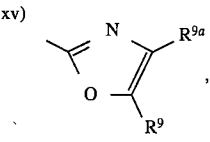

xvi) 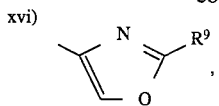

xvii) 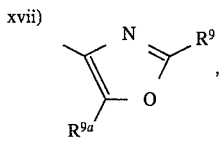

xviii) 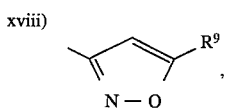

xix) 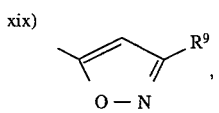

xx) 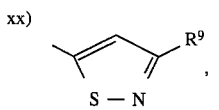

xxi) 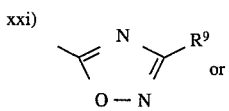

xxii) 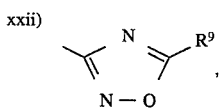

and the other symbols have the same meaning as hereinbefore defined, (xix) by esterification of a compound obtained by hereinbefore reaction (iv), (v) or (xviii) of formula (Ib):

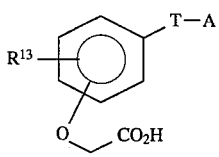 (Ib)

wherein all the symbols have the same meaning as hereinbefore defined, with a compound of formula (o):

OH                                                    (o)

wherein $R^{10b}$ is C1–12 alkyl, or (xx) by amidation of a compound obtained hereinbefore by reaction (iv), (v), or xviii) of the formula (Ib):

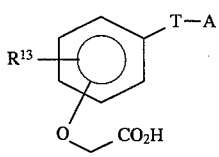 (Ib)

wherein all the symbols have the same meaning as hereinbefore defined, with a compound of formula (p):

NH                                                (p)

wherein all the symbols have the same meaning as hereinbefore defined.

The reaction (i) is known, for example, it may be carried out in an inert organic solvent (tetrahydrofuran (THF),  methanol, ethanol, dimethoxyethane, dioxane or mixing thereof, etc.) at 0°–70° C.

The reactions (ii) and (viii) are known, for example, they may be carried out in a water miscible organic solvent (THF, dioxane, methanol, ethanol, dimethoxyethane mixtures thereof, etc.), in the presence of an acid (hydrochloric acid, acetic acid, trifluoroacetic acid, etc.) using a reducing agent (sodium cyanoborohydride etc.) at 0°–70° C.

The reactions (iii) and (vi) are known, for example, they may be carried out in an inert organic solvent (methylene chloride, etc.) in the presence of an appropriate condensing agent (2-chloro-N-methylpyridinum iodide etc.) and a proper base (triethylamine N,N-dimethylaminopyridine or mixtures thereof, etc.) at 0°–40° C.

The (iv) is known, for example, it may be carried out in acetone using a Jone's agent at −10°–40° C.

The reaction (v) is known, for example, it may be carried out in an inert organic solvent (THF, diethylether, dioxane, ethyl acetate, methanol, ethanol, methylene chloride etc.) using a catalyst (palladium on carbon, palladium, hydoxy palladium, palladium acetic acid, palladium black, platinum black etc.) at normal or elevated pressures of hydrogen gas, at 0°–80° C.

The reaction may be carried out, for the convenience of purification by exposing a compound of formula (Ib-1) to methylestification and to hydrogenation, following hydrolysis of an ester bond. The methylestification is known, for example, it may be carried out in an inert organic solvent (diethylether ethyl acetate, etc.) using diazomethane at 0°–10° C. The hydolysis of an ester bond may be carried out by the same procedure as hereafter defined for reaction (xviii).

The reaction (vii) is known, for example, it may be carried out in an inert organic solvent (methanol ethanol, etc.) under an atmosphere of inert gas at 0°–40° C.

The reaction (ix) is known, for example, it may be carried out in an inert organic solvent (N,N-dimethylformamide (DMF), etc.) in the presence or absence of an appropriate base (sodium hydride etc.).

The reaction (x) is known, for example, it may be carried out in an inert organic solvent (chloroform, cyclohexane, or mixtures thereof, etc.), in the presence of a Lewis acid (trifluoroborane etherate, etc.), or in an inert organic solvent (DMF etc.), in the presence of an amine (N,N-dimethylaminopyridine triethylamine pyridine etc.) at 0° C.—a reflux temperature.

The reaction (xi) is known for example it may be carried out in an inert organic solvent (methylene chloride, etc.), in the presence of an appropriate condensing agent (2-chloro-N-methylpyridinum iodide etc.) and a proper base (triethylamine, N,N-dimethylaminopyridine, mixtures thereof etc.) at 0°–40° C.

The reaction (xii) is known, for example, it may be carried out in inert organic solvent (DMF, THF, etc.) in the presence of an appropriate base (sodium hydride, potassium t-butoxide n-butyllithium, etc.).

The reaction (xiii) is known, for example, it may be carried out in an inert organic solvent (chloroform etc.) at 0° C.—a reflux temperature.

The reaction (xiv) is known, for example, it may be carried out in an inert organic solvent (DMF, acetone, etc.) in the presence of an appropriate base (potassium carbonate etc.) at 0°–50° C.

The reaction (xv) is known, it may be carried out at 80°–135° C. without an organic solvent.

The reaction (xvi) and (xvii) are known, for example, they may be carried out in an inert organic solvent (truene, etc.) at 0° C.—a reflux temperature.

The reaction (xviii) is known, for example, it may be carried out in an inert organic solvent (methanol, ethanol, dioxane, THF, dimethoxyethane mixtures thereof etc.) using an alkali solution (potassium hydroxide, sodium hydroxide, potassium carbonate, sodium carbonate etc.) at 0°–50° C.

The reactions (xix) and (xx) are known, for example, they may be carried out in an inert organic solvent (methylene chloride etc.) with an acyl halide such as oxalyl chloride and thionyl chloride, and then by reacting a compound thus obtained with an alcohol of formula (o) or an amine of formula (p), respecitvely in an inert organic solvent (methylene chloride, etc.), in the presence of an appropriate base (triethylamine etc.) at 0°–40° C.

Compounds of the formulae (III), (VI), (VIII), (IX), (X), (XII), (XIV), (XV), (XVII), (XVIII) and (XX) may be prepared using a series of reactions depicted in the following schemes.

Scheme [A]

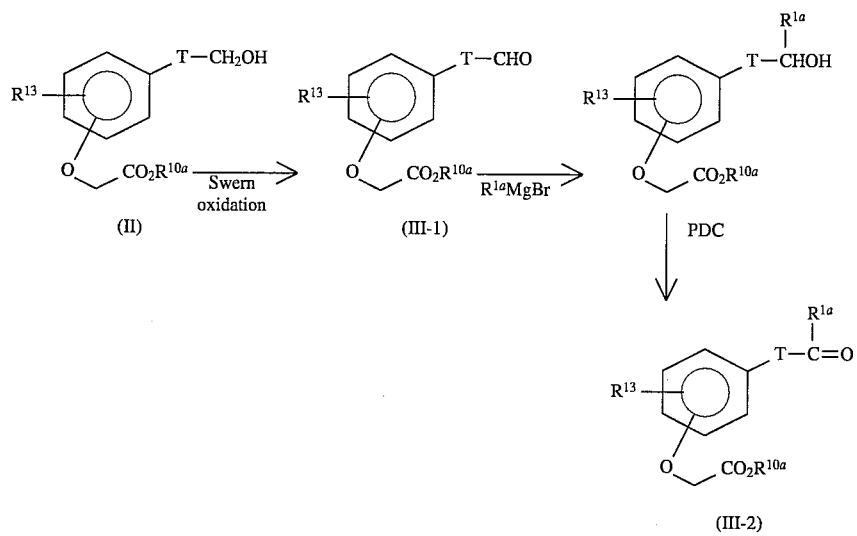

Scheme [B]

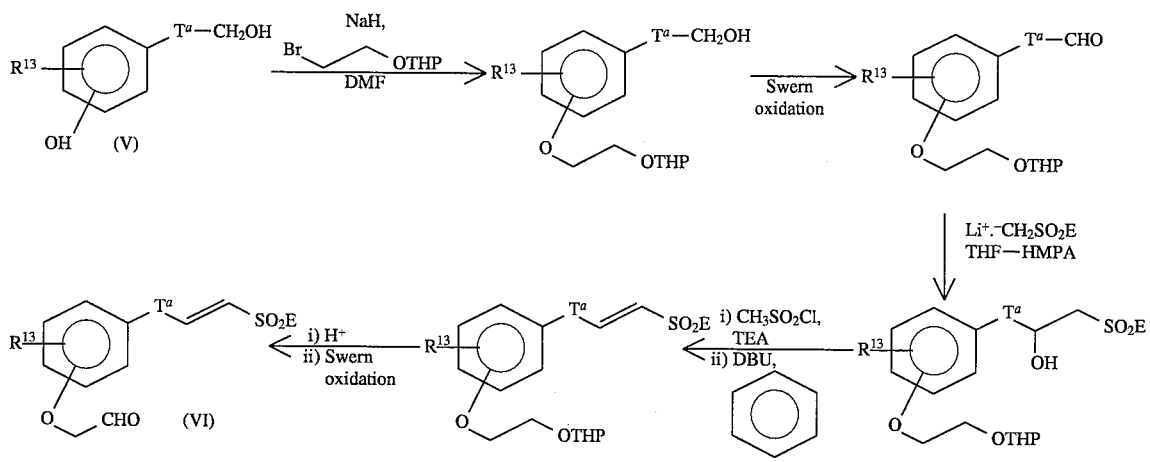

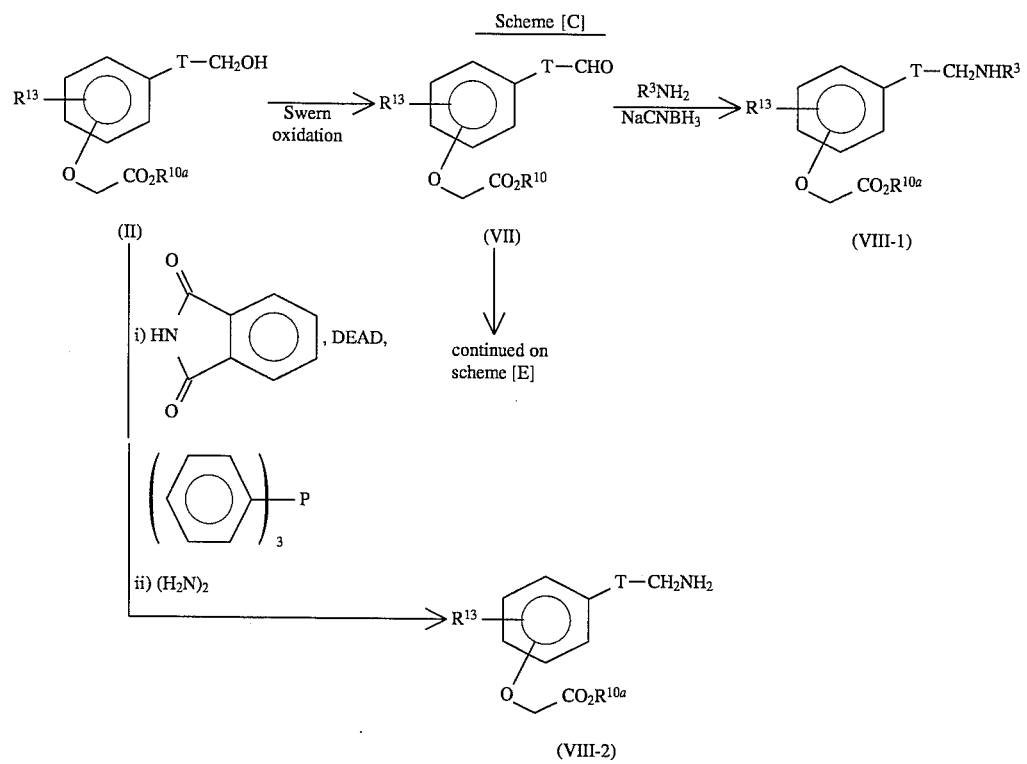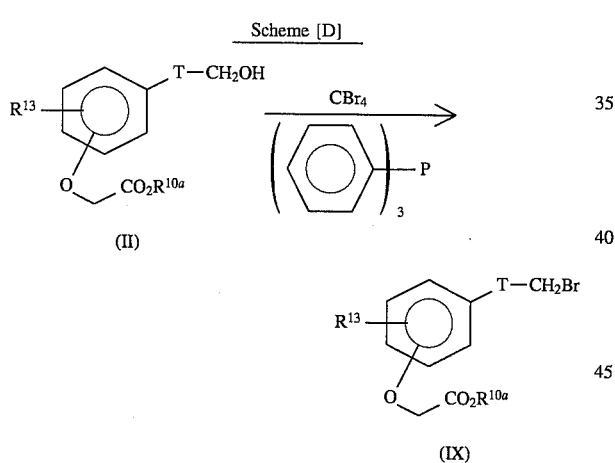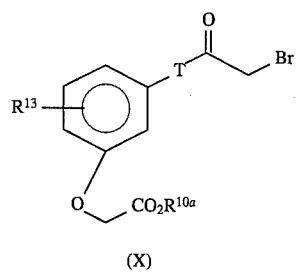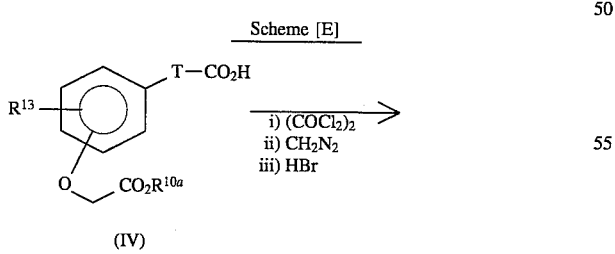

Scheme [F]
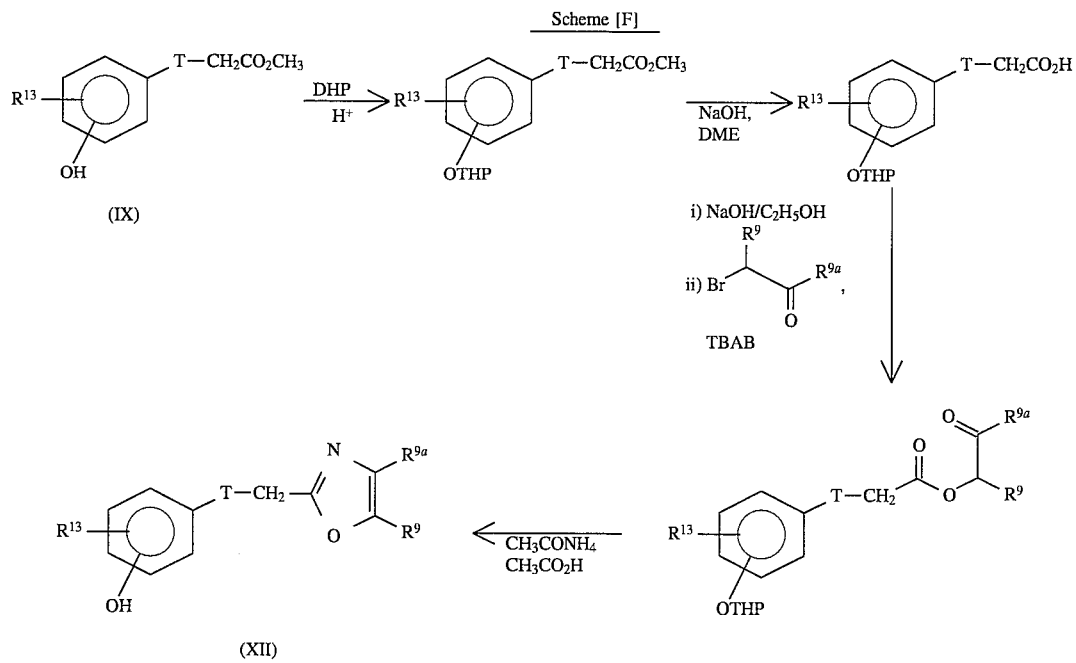
Scheme [G-1]
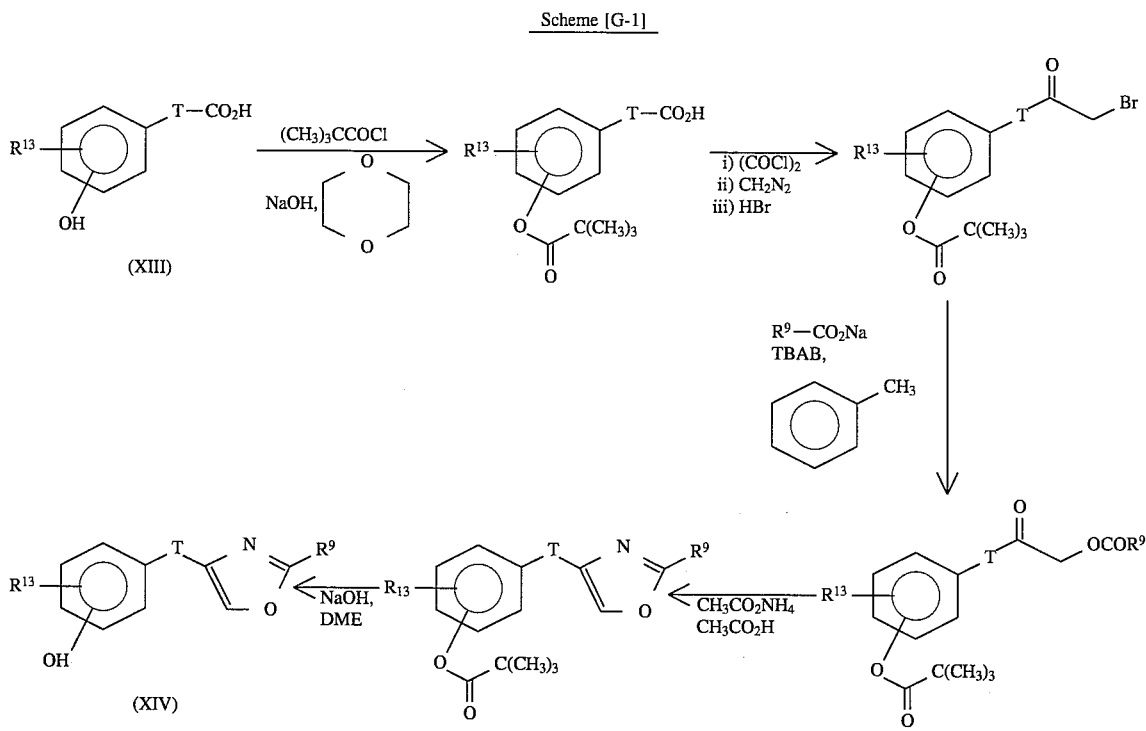

Scheme [G-2]
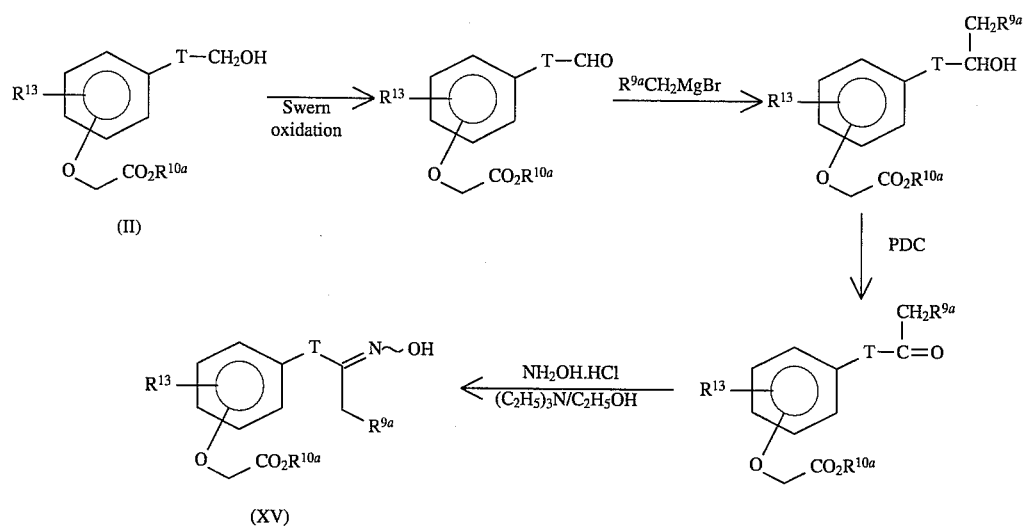

Scheme [H]
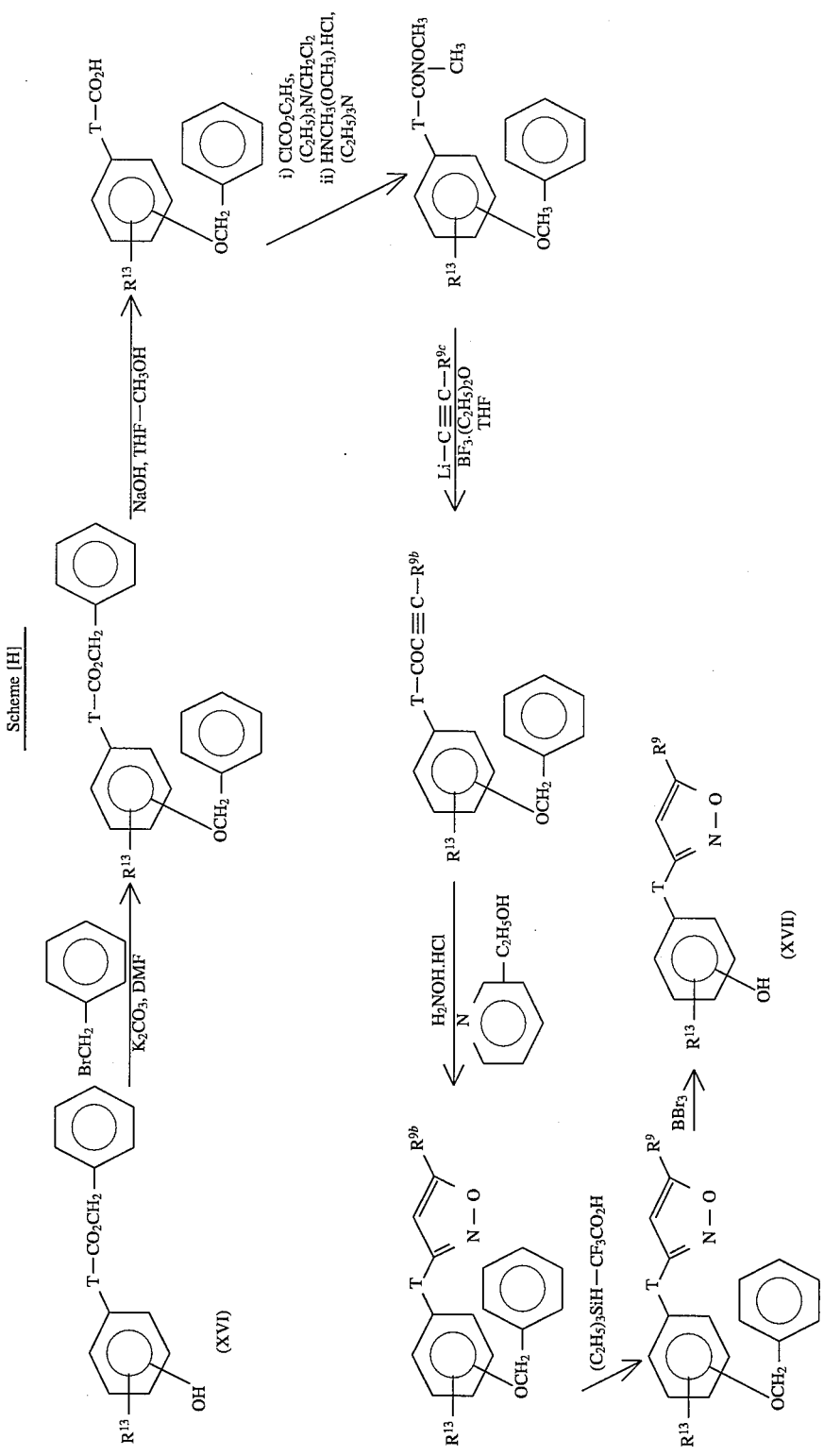

Scheme [I]

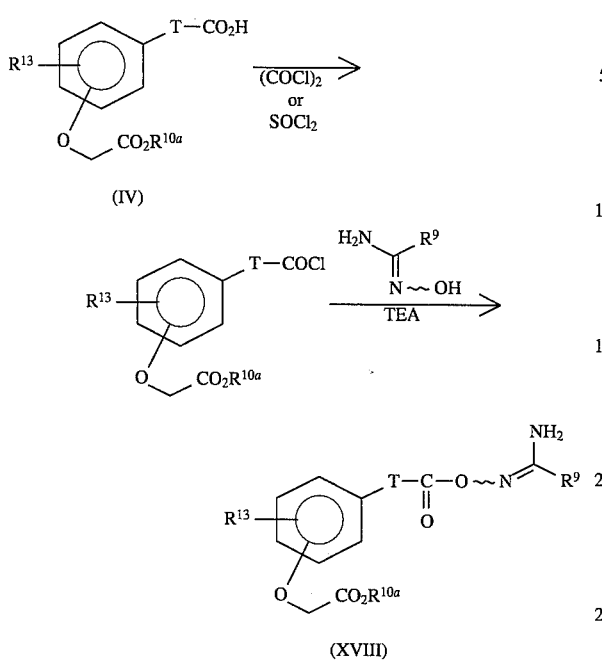

SCHEME [J]

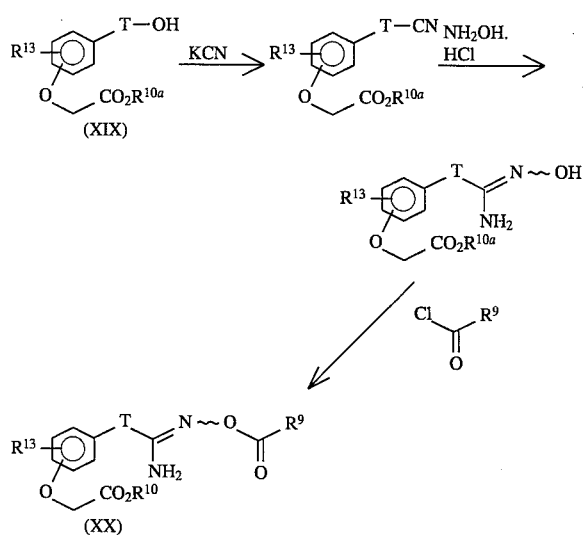

In the schemes, $R^{9b}$ is (i) hydrogen, (ii) phenyl, (iii) C1–4 alkyl or (iv) C1–4 alkyl substituted by one or two rings optionally selected from phenyl or 4–7 membered monocyclic hetero ring containing one nitrogen and/or one hydroxy;

$R^{9c}$ has same meaning as $R^{9b}$ provided that the hydroxy in $R^{9b}$ is replaced by —OLi;

and the other symbols have the same meaning as hereinbefore defined;

PDC is pridinum dichlomate;

THP is tetrahydropyran-2-yl;

DMF is N,N-dimethylformamide;

THF is tetrahydrofuran;

HMPA is hexamethylphosphoramide;

TEA is triethylamine;

DBU is 1,8-diazabicyclo [5, 4, 0]-7-undecene;

DEAD is diethylazocarboxylate;

DHP is dihydropyran;

DME is dimethoxyethane; and

TBAB is n-tetrabutylammonium bromide.

In each reaction in the instant specification, products may be purified by a conventional manner. For example, it may be carried out by distillation at atmospheric or reduced pressure, high performace liquid chromatography, thin layer chromatography or column chromatography using silica gel or magnesium silicate, washing or recrystallization. Purification may be carried out after each reaction or after a series of reactions.

The starting materials and reagents in processes for preparing the instant compounds are known per se, or may be prepared by methods known per se.

PHARMACOLOGIC ACTIVITIES

It has been confirmed that the compounds of the instant invention of formula (I) possess an agonistic activity at the $PGI_2$ receptor by the following experimental results.

i) Inhibitory activity on binding of [$^3$H]-iloprost to $PGI_2$ receptor in the human blood platelet membrane fraction Method 50 mM Tris-HCl buffer (pH 7.4) containing 15 mM $MgCl_2$, 5 mM EDTA and 10 nM [$^3$H]-iloprost were used as reaction medium. To 0.2 ml of the reaction medium, human blood platelet membrane fraction (0.3 mg protein) was added with or without a test compound. The mixture was incubated at 24° C. for 30 min. After incubation, 4 ml of ice-cold 10 mM Tris-HCl buffer (pH 7.4) was added to the reaction mixture, the mixture was filtered through Whatman GF/B glass fiber filter, and washed 4 times with 4 ml of ice-cold 10 mM Tri-HCl buffer (pH 7.4) to separate bound and free [$^3$H]-iloprost. After washing, the filter was dried and radioactivity was counted. Non-specific binding was obtained by performing parallel binding experiments in the presence of 10 μM non-labelled iloprost. Specific binding was calculated by subtracting the non-specific binding from the total binding.

The inhibitory effect of a test compound was calculated from the following equation.

The percentage of inhibition (%)=100−($B_1/B_0$×100)

$B_1$: specific [$^3$H]-iloprost binding in presence of test compound $B_0$: specific [$^3$H]-iloprost binding in the absence of a test compound The results are shown in the following Table 1.

TABLE 1

| Example No. | $IC_{50}$ (μM) |
|---|---|
| 2 | 4.8 |
| 4 | 1.6 |
| 6 | 3.0 |
| 8(l) | 1.5 |
| 8(n) | 2.0 |
| 8(o) | 0.46 |
| 12 | 1.3 |
| 15 | 4.0 |
| 17 | 0.15 |
| 17(b) | 0.36 |
| 17(c) | 0.27 |
| 17(i) | 0.22 |

TABLE 1-continued

| Example No. | IC$_{50}$ (μM) |
|---|---|
| 17(n) | 2.0 |
| 17(s) | 0.78 |
| 17(x) | 5.0 |
| 17(cc) | 0.26 |
| 19 | 0.12 |
| 21 | 4.4 |
| 23 | 1.5 | ii) Inhibitory effect on human blood platelet aggregation

Method

Platelet-rich plasma (PRP) was prepared from human blood ($5\times10^5$ platelets/mm$^3$) and a test compound was added to PRP 1 minute prior to the addition of ADP (4 μm). The aggregation was monitored using a platelet aggregometer (NBS HEMA TRACER 601, Niko Bioscience, Japan).

The results are shown in the following Table 2.

TABLE 2

| Example No. | IC$_{50}$ (μM) |
|---|---|
| 4 | 3.7 |
| 8(n) | 3.1 |
| 8(o) | 0.97 |
| 12 | 5.0 |
| 17 | 0.42 |
| 17(b) | 0.24 |
| 17(c) | 0.47 |
| 17(s) | 3.2 |
| 17(cc) | 0.41 |
| 19 | 0.16 |
| 23 | 0.37 |

Toxicity

The toxicity of the compounds of the instant invention of the formula (I) is very low and therefore, it may be confirmed that the compounds of the instant invention are fully safe for pharmaceutic use.

APPLICATION FOR PHARMACEUTICS

The compounds of the instant invention of formula (I) possess an agonistic activity on the PGI$_2$ receptor and therefore are useful for the prevention and/or the treatment of thrombosis, arteriosclerosis, ischemic heart diseases, gastric ulcer and hypertension etc.

For the purpose described above the compounds of formula (I) of the instant invention, non-toxic salts thereof, acid additional salts thereof and hydrates thereof may be administered normally systemically or partially, usually by oral or parenteral administration.

The doses to be administered are determined depending on age, body weight, symptom, the desired therapeutic effect, the route of administration, the duration of the treatment etc. In the human adult, the doses per person per dose are generally between 1 mg and 1000 mg, by oral administration, up to several times per day, and between 100 μg and 100 mg, by parenteral administration up to several times per day, or continuous administration between 1 and 24 hrs. per day via a vein.

As mentioned above, the doses to be used depend on various conditions. Therefore, there are cases in which doses lower than or greater than the ranges specified above may be used.

When administering a compound of the instant invention, it is used as solid compositions, liquid compositions, other compositions for oral administration, as liniments as suppositories etc. for parenteral administration.

Solid compositions for oral administration include compressed tablets, pills, capsules, dispersible powders and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate etc.). The compositions also may comprise, as is normal practice, additional substances other than inert diluents: e.g. lubricating agents (such as magnesium stearate etc.) disintegrating agents (such as cellulose calcium glycolate, etc.), stabilizing agents (such as lactose etc.), and assisting agents for dissolving such as glutamic acid, etc.).

The tablets, pills may, if desired, be coated with a film of gastric or enteric material (such as sugar gelatin, hydroxypropyl cellulose or may hydroxypropylmethyl cellulose phtalate, etc.), or may be coated with more than two films. Further, coating may include containment within capsules of absorbable materials such as gelatin.

Liquid compositions for oral administration include pharmaceutically-acceptable solutions, emulsions, suspensions, syrups and elixirs. In such compositions, one or more of the acitve compound(s) is or are contained in inert diluent(s) commonly used in the art (Purified water, ethanol etc.). Besides inert diluents, such compositions also may comprise adjuvants (such as wetting agents, suspending agents, etc.) sweetening agents, flavouring agents, perfuming agents and preserving agents.

Other compositions for oral administration included spray compositions which may be prepared by known methods and which comprise one or more of the active compound(s). Spray compositions may comprise additional substances other than inert diluents: e.g. stabilizing agents (sodium sulfate etc.), isotonic buffer(sodium chloride, sodium citrate, citric acid etc.). For preparation of such spray compositions, for example, the method described in U.S. Pat. Nos. 2,868, 691 or 3,095,355 (herein incorporated entirety by reference) may be used.

Injections for parenteral administration include sterile aqueous or non-aqueous solutions, suspensions and emulsions. In such compositions, one more of active compounds(s) is or are admixed with at least one of inert aqueous diluent(s) (distilled water for injection, physiological salt solution etc.) or inert non-aqueous diluent(s) (propylene glycol, polyethylene glycol, olive oil, ethanol, POLYSORBATE80 (registered trade mark) etc.).

Injections may comprise additional other inert diluents: e.g. preserving agents, wetting agents, emulsifying agents, dispersing agents, stabilizing agent (lactose, etc.), assisting agents such as assisting agents for dissolving (glutamic acid, asparaginic acid, etc.).

They may be sterilized for example, by filtration through a bacteria-retaining filter, by incorporation of sterilizing agents in the compositions or by irradiation. They also may be manufactured in the form of sterile solid compositions, for example, by freeze-drying, and which may be dissolved in sterile water or some other sterile diluent(s) for injection immediately before use.

Other compositions for parenteral administration include liquids for external use, endermic liniments, ointment, suppositories and pessaries which comprise one or more of the active compound(s) and may be prepared by per se known methods.

REFERENCE EXAMPLES AND EXAMPLES

The following reference examples and examples illustrate the instant invention, but do not limit the present invention.

The solvents in parentheses show the developing or eluting solvents and the ratios of the solvents used are by volume in chromatographic separations.

Unless otherwise specified, "IR" were measured by the liquid film method and "NMR" were measured in a solution of CDCl$_3$.

Reference Example 1

Methyl 3-(3-formylpropyl)phenoxyacetate

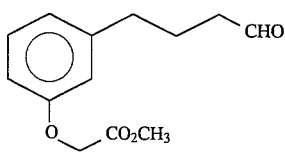

To a solution of oxalyl chloride (1.26 ml) in methylene chloride (30 ml) at −70° C., a solution of dimethylsulfoxide (2.11 ml) in methylene chloride (3.0 ml) was added dropwise. To the obtained solution, a solution of methyl 3-(4-hydroxybutyl) phenoxyacetate (1.94 g) in methylene chloride (8.0 ml) was added dropwise. Triethylamine (6.9 ml) was added dropwise thereto while the reaction temperature was maintained at −70° C. The reaction mixture was warmed slowly to −40° C. over a 30 min period and then quenched by addition of a saturated aqueous solution of ammonium chloride. The reaction mixture was extracted with ether. The extract was washed with a saturated aqueous solution of ammonium chloride and a saturated aqueous solution of sodium chloride, successively, dried over anhydrous magnesium sulfate and evaporated. The residue was purified by silica gel column chromatography (n-hexane:ethyl acetate=5:2) to give the title compound (1.41 g) having the following physical data.

TLC: Rf 0.26 (nohexane:ethyl acetate=2:1); NMR: δ9.74 (1H, s), 7.35-7.07(1H, m), 6.92-6.60 (3H, m), 4.62 (2H, s), 3.79 (3H, s), 2.63 (2H, t, J=7Hz), 2.47 (2H, t, J=8Hz), 2.10-1.92 (2H, m).

Reference Example 2

Methyl 3-(4-hydroxyheptyl)phenoxyacetate

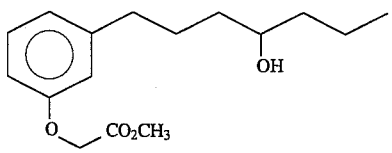

To a solution of the compound prepared in reference example 1 (1.26 g) in diethyl ether (10 ml), n-propylmagnesium bromide (3.0 ml of 2M in diethyl ether) was added dropwise at −78° C. The reaction mixture was stirred for 2 h with warming. After being quenched by addition of a saturated aqueous solution of ammonium chloride, the mixture was extracted with ether. The extract was washed with a saturated aqueous solution of sodium chloride, dried over anhydrous magnesium sulfate, and evaporated. The residue was purified by silica gel column chromatography (n-hexane:ethyl acetate=2:1) to give the title compound (820 mg) having the following physical data.

TLC: Rf 0.23 (n-hexane:ethyl acetate=2:1); NMR: δ7.36-7.08 (1H, m), 6.95-6.60 (3H, m), 4.64 (2H, s), 3.82 (3H, s), 3.80-3.50 (1H, m), 2.80-2.36 (3H, m), 2.20-1.25 (8H, m), 1.10-0.80 ( 3H, m).

Reference Example 3

Methyl 3-(4-oxoheptyl)phenoxyacetate

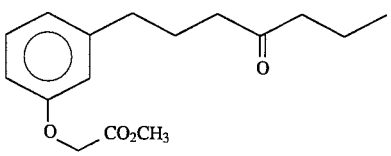

Pyridium dichromate (2.53 g) was added to a solution of the compound prepared in reference example 2 (750 mg) in dimethylformamide (10 ml) at room temperature. The mixture was stirred overnight. Celite (registered trade mark) and Florisil (registerd trade mark) were added to the mixture. The mixture was diluted with a mixture of n-hexane-ethyl acetate (3:1)(20 ml). The mixture was filtered through Florisil, and the filtrate was evaporated. The residue was purified by silica gel column chromatography (n-hexane:ethyl acetate=5:1) to give the title compound (350 mg) having the following physical data.

TLC: Rf 0.30 (n-hexane:ethyl acetate=3:1); NMR: δ7.36-7.08 (1H, m), 6.90-6.60 (3H, m), 4.62 (2H, s), 3.81 (3H, s), 2.72-2.25 (6H, m), 2.10-1.38 (4H, m), 0.90 (3H, t, J=8Hz).

Reference Example 4

3-[3-[2-(tetrahydropyran-2-yl)oxyethoxy]phenyl]propanol

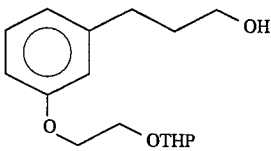

To a suspension of sodium hydride (1.84 g, 60% dispersion) in dimethylformamide (50 ml) was added dropwise a solution of 3-(3-hydroxypropyl)phenol (7.0 g) in dimethylformamide (20 ml) at 0° C. The mixture was stirred for 1 h at room temperature. To the reaction mixture was added 1-bromo-2-(tetrahydropyran-2-yl)ethane (5.46 g) at 0° C. The mixture was stirred for 1 h at room temperature. After being quenched by addition of water, the mixture was extracted with ether. The extract was washed with 2N aqueous solution of sodium hydroxide, water and a saturated aqueous solution of sodium chloride, successively, dried over anhydrous magnesium sulfate, and evaporated. The residue was purified by silica gel column chromatography (ethyl acetate:n-hexane=1:2→2:1) to give the title compound (3.36 g) having the following physical data.

TLC: Rf 0.17 (ethyl acetate:n-hexane=1:2); IR(cm$^{-1}$): v3369, 2930, 1584, 1488, 1451, 1384, 1353, 1260, 1202, 1125, 1034, 992, 874, 814, 777, 695.

Reference Example 5

1-[2-(Tetrahydropyran-2-yl)oxyethoxy]-3-(3-hydroxy-4-diphenylamino sulfonylbutyl)benzene

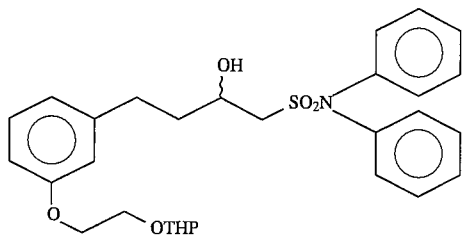

To a solution of N,N-diphenylsulfonamide (0.99 g) in a mixture of tetrahydrofuran-hexamethylphosphoramide (20:3) (23 ml) was added dropwise n-butyllithium (3.75 ml of 1.6M in n-hexane) at −78° C. The mixture was stirred for 30 min at −78° C. To the mixture obtained was added a solution of a compound (which was prepared by the same procedure as reference example 1, using the compound prepared in reference example 4) (1.11 g) in tetrahydrofuran (10 ml). The reaction mixture was stirred for 1 h at −78° C. After quenched by addition of water, the mixture was extracted with ethyl acetate. The extract was washed with water and a saturated aqueous solution of sodium chloride, successively, dried over anhydrous magnesium sulfate and evaporated. The residue was purified by silica gel column chromatography (ethyl acetate:n-hexane=1:2) to give the title compound (0.84 g) having the following physical data.

TLC: Rf 0.37 (ethyl acetate:benzene=1:1); IR(cm$^{-1}$): v3401, 3063, 2930, 1586, 1489, 1451, 1351, 1261, 1190, 1150, 1077, 1050, 1011, 969, 903, 822, 757, 697.

Reference Example 6

1-[2-(Tetrahydropyran-2-yl)oxyethoxy]-3-(3-methylsulfonyloxy-4-diphenylaminosulfonyl)benzene

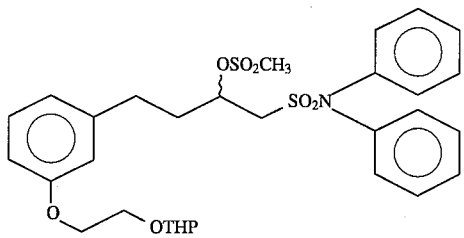

To a solution of the compound prepared in reference example 5 (0.66 g) in methylene chloride (20 ml) were added successively triethylamine (0.305 g), methanesulfonyl chloride (0.12 ml) at 0° C. The mixture was stirred for 10 min at same temperature. After quenched by addition of water, the mixture was extracted with ethyl acetate. The extract was washed with a saturated aqueous solution of ammonium chloride, water and a saturated aqueous solution of sodium chloride successively dried over anhydrous magnesium sulfate, and evaporated. The residue containing the title compound having the following physical data. The residue was used for the next reaction without further purification.

TLC: Rf 0.31 (ethyl acetate:benzene=1:8).

Reference Example 7

1-[2-(Tetrahydropyran-2-yl)oxyethoxy]-3-(4-diphenylaminosulfonyl-3butenyl)benzene

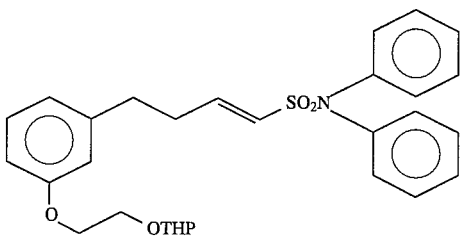

To a solution of the residue obtained in reference example 6 in benzene was added 1, 8-diazabicyclo[5, 4, 0]-7-undecene (0.382 g) at 0° C. The mixture was stirred for 10 min at 0° C. After quenched by addition of water, the mixture was extracted with ethyl acetate. The extract was washed with a saturated aqueous solution of sodium ammonium, water and a saturated aqueous solution of sodium chloride, successively, dried over anhydrous magnesium sulfate and evaporated to give the title compound (0.63 g) having the following physical data.

TLC: Rf 0.27 (ethyl acetate:benzene=1:8); IR (cm$^{-1}$): v3063, 2943, 2873, 1734, 1586, 1489, 1451, 1354, 1260, 1152, 1126, 1076, 1034, 989, 969, 904, 874, 816, 757, 697.

Reference Example 8

2-[3-(4-Diphenylaminosufonyl-3-butenyl)phenoxy]ethanol

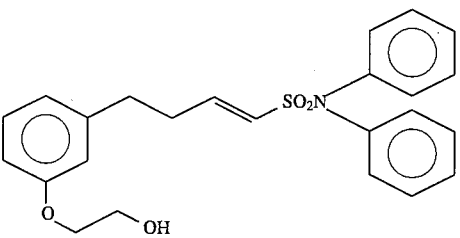

To a solution of the compound prepared in reference example 7 (0.541 g) in methanol (20 ml) was added a catalytic amount of 10-camphorsulfonic acid (dl form) at room temperature. The mixture was stirred for 1 h at room temperature. To the reaction mixture was added triethylamine (0.1 ml) and the mixture was evaporated. The residue was purified by silica gel column chromatography (ethyl acetate:n-hexane=1:2→1:1) to give the title compound (0.404 g) having the following physical data.

TLC: Rf 0.37 (ethyl acetate:benzene=1:1); IR(cm$^{-1}$): v3401, 3063, 2930, 1586, 1489, 1451, 1351, 1261, 1190, 1150, 1077, 1050, 1011, 969, 903, 822, 757, 697.

Reference Example 9

Methyl 3-(3-bromopropyl)phenoxyacetate

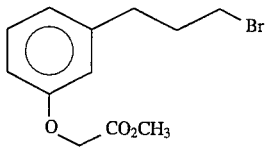

To a stirred solution of methyl 3-(3-hydroxypropyl)phenoxyacetate (2.00 g) in methylene chloride (20 ml) were added successively triphenylphosphine (2.81 g) and tetrabromomethane (3.55 g) at room temperature. The mixture was evaporated. The residue was purified by silica gel column chromatography (n-hexane:ethyl acetate=7:1) to give the title compound (1.69 g) having the following physical data.

TLC: Rf 0.26 (n-hexane:ethyl acetate=2:1); NMR: δ7.30-7.06 (1H, m), 6.90-6.60 (3H, m), 4.63 (2H, s), 3.81 (3H, s), 3.38 (2H, t, J=8Hz), 2.76 (2H, t, J=8Hz), 2.32-1.96 (2H, m).

Reference Example 10

1-Benzyloxy-3-(3-benzyloxycarbonylpropyl)benzene

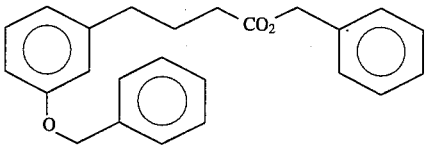

A mixture of 1-hydroxy-3-(3-benzyloxycarbonylpropyl)benzene (2.0 g), benzylbromide (1.14 ml), potassium bicabonate (1.53 g) and dimethylformamide (20 ml) was stirred for 3 h at room temperature. The mixture was quenched by addition of water and extracted with a mixture of n-hexane:ethyl acetate (3:1). The extract was washed with water and a saturated aqueous solution of sodium chloride successively, dried over anhydrous magnesium sulfate, and evaporated. The residue was purified by silica gel column chromatography (n-hexane:ethyl acetate=10:1) to give the title compound (2.55 g) having the following physical data.

TLC: Rf 0.33 (n-hexane:ethyl acetate=7:1); IR(cm$^{-1}$): ν3065, 3033, 2939, 2866, 1734, 1583, 1489, 1455, 1382, 1315, 1258, 1156, 1082, 1027, 908, 850, 777, 739.

Reference Example 11

4-(3-Benzyloxyphenyl)butanoic acid

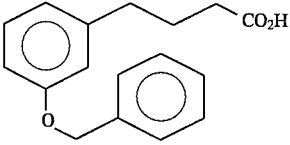

To a solution of the compound prepared in reference example 10 (2.42 g) in a mixture of tetrahydrofuran-methanol (2:1) (20 ml) was added 2N aqueous solution of sodium hydroxide (11 ml) at 0° C. The mixture was stirred for 3 h at room temperature. After neutralized by addition of 2N aqueous solution of hydrochloric acid, the mixture was extracted with ethyl acetate. The extract was washed with water and a saturated aqueous solution of sodium chloride, successively, dried over anhydrous magnesium sulfate and evaporated. The residue was recrystallized from n-hexane-ethyl acetate to give the title compound (1.5 g) having the following physical data.

mp.: 100.0°–102.0° C.; TLC: Rf 0.53 (ethyl acetate); NMR: δ7.50-7.08 (7H, m), 6.93-6.70 (3H, m), 5.04 (2H, s), 2.66 (2H, t, J=7Hz), 2.36 (2H, t, J=8Hz), 2.16-1.93 (2H, m).

Reference Example 12

1-Benzyloxy-3-[3-(N-methyl-N-methoxyamino)carbonylpropyl]benzene

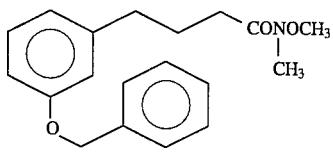

An ethyl chloroformate (0.96 ml) was dissolved with stirring of a solution of the compound prepared in reference example 11 (2.45 g) and triethylamine (1.35 ml) in methylene chloride (30 ml) at −10° C. After stirred for 10 min at room temperature, to the mixture were added successively triethylamine (2.8 ml) and N-methyl-N-methoxyamine hydrochloride (980 mg) at −10° C. The mixture was stirred further for 1 h at room temperature and was poured into water. The mixture was extracted with a mixture of n-hexane-ethyl acetate (1:1). The extract was washed with water and a saturated aqueous solution of sodium chloride, successively, dried over anhydrous magnesium sulfate and evaporated. The residue was purified by silica gel column chromatography (n-hexane:ethyl acetate=2:1) to give the title compound (2.67 g) having the following physical data.

TLC: Rf 0.23 (n-hexane:ethyl acetate=2:1); NMR: δ5 7.48-7.03 (6H, m), 6.86-6.67 (3H, m), 5.04 (2H, s), 3.61 (3H, s), 3.16 (3H, s), 2.78-2.30 (4H, m), 2.12-1.80 (2H, m).

Reference Example 13

1-Benzyloxy-3-(3-hydroxy-3,3-diphenyl-1-propynyl)carbonylpropyl benzene

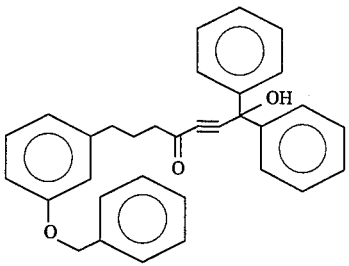

To a solution of 1,1-diphenyl-2-propyn-1-ol (3.89 g) in tetrahydrofuran (40 ml) was added n-butyllithium (23.4 ml of 1.6M in n-hexane) at −78° C. After being stirred for 30 min at the same temperature, to the mixture was added boron trifluoride etherate (5.05 ml). The mixture was stirred for 30 min at −78° C. To the mixture, the compound prepared in reference example 12 (2.67 g) in tetrahydrofuran (20 ml) was added at same temperature. After being stirred for 1 h at −78° C. the reaction mixture was quenched by addition of a saturated aqueous solution of ammonium chloride and the mixture stirred for 30 min at room temperature. The mixture was extracted with a mixture of n-hexane-ethyl acetate (3:1). The extract was washed with water and a saturated aqueous solution of sodium chloride, successively, dried over anhydrous magnesium sulfate and evaporated. The residue was purified by silica gel column chromatography (n-hexane-:ethyl acetate=7:1) to give the title compound (2.8 g) having the following physical data.

mp.: 54.5°–56.0° C. TLC: Rf 0.18 (n-hexane:ethyl acetate=6:1); NMR: δ7.45-7.10 (16H, m), 6.86-6.71 (3H, m), 5.01 (2H, s), 3.00 (1H, s), 2.68-2.53 (4H, m), 2.10-1.90 (2H, m).

Reference Example 14

1-Benzyloxy-3-[3-(5-hydroxydiphenylmethylisoxazole-3-yl)propyl]benzene

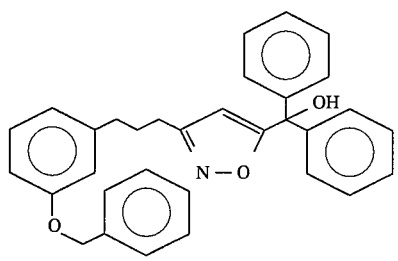

A mixture of the compound prepared in reference example 13 (1.0 g), hydroxyamine hydrochloride (1.5 g) and pyridine (10 ml) and ethanol (10 ml) was refluxed for 6 h. The mixture was concentrated under reduced pressure, the reside was quenched by addition of water. The mixture was extracted with ethyl acetate. The extract was washed with a saturated aqueous solution of sodium chloride, dried over anhydrous magnesium sulfate and evaporated. The residue was purified by silica gel column chromatography (n-hexane:ethyl acetate=7:1) to give the title compound (940 mg) having the following physical data.

mp.: 89.0°–90.5° C.; NMR: δ7.43-7.16 (16H, m), 6.80-6.74 (3H, m), 5.80 (1H, s), 5.03 (2H, s), 3.17 (1H, s), 2.67-2.61 (4H, m), 2.00-1.90 (2H, m).

Reference Example 15

1-Benzyloxy-3-[3-(5-diphenylmethylisoxazol-3-yl)propyl]benzene

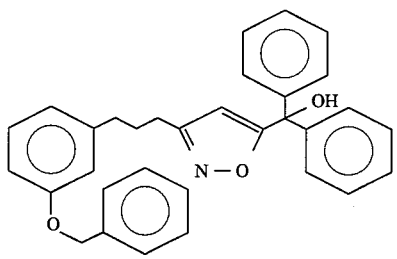

To a solution of the compound prepared in reference example 14 (860 mg) in trifluoroacetic acid (8.0 ml) was added a solution of triethylsilane (440 mg) in methylene chloride (2.0 ml) with stirring at 0° C. After stirred for 30 min at room temperature, the mixture was concentrated under reduced pressure. The residue was neutralized with a saturated aqueous solution of sodium bicarbonate and extracted with ethyl acetate. The extract was washed with water and a saturated aqueous solution of sodium chloride successively, dried over anhydrous magnesium sulfate, and evaporated. The residue was purified by silica gel column chromatography (n-hexane:ethyl acetate=8:1) to give the title compound (640 mg) having the following physical data.

TLC: Rf 0.50 (n-hexane:ethyl acetate=3:1); NMR: δ7.50-7.00 (16H, m), 6.85-6.65 (3H, m), 5.70 (1H, s), 5.30 (1H, s), 5.03 (2H, s), 2.80-2.50 (4H, m), 2.17-1.75 (2H, m).

Reference Example 16

1-Hydroxy-3-[3-(5-diphenylmethylisoxazol-3-yl)propyl]benzene

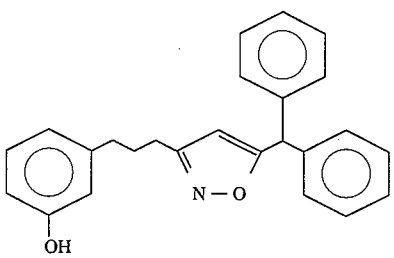

To a solution of the compound prepared in reference example 15 (550 mg) in methylene chloride (6.0 ml) was added boron tribromide (0.34 ml) with stirring at 0° C. The mixture was stirred for 30 min at 0° C., and poured into ice water and extracted with ethyl acetate. The extract was washed with water and a saturated aqueous solution of sodium chloride successively, dried over anhydrous magnesium sulfate, and evaporated. The residue was purified by silica gel column chromatography (n-hexane:ethyl acetate= 5:1→3:1) to give the title compound (376 mg) having the following physical data.

mp.: 114.5°–117° C.; TLC: Rf 0.22 (n-hexane:ethyl acetate=3:1); NMR: δ7.39-7.05 (11H, m), 6.75-6.60(3H, m), 5.73 (1H, s), 5.62-5.53 (1H, m), 5.52 (1H, s), 2.70-2.52 (4H, m), 2.02-1.84 (2H, m).

Reference Example 17

Methyl 3-[3-[(1-amino-2,2-diphenylethylidene)aminooxycarbonyl]propyl]phenoxyacetate

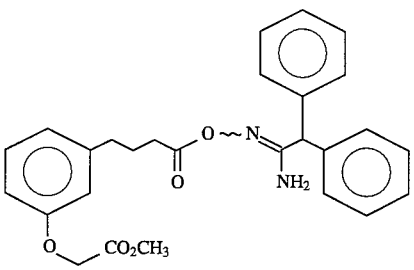

A suspension of 4-(3-methoxycarbonylmethoxyphenyl-)butanoic acid (289 mg) and thionyl chloride (5.0 ml) was refluxed for 1 h. The mixture was cooled to room temperature and concentrated under reduced pressure. To a suspension of the residue and 1,1-diphenyl-2-amino-2-hydroxyiminoethane (285 mg) in methylene chloride (5 ml) was added tiethylamine (0.32 ml) with stirring at room temperature. The mixture was stirred overnight at room temperature. After quenched by addition of water, the mixture was extracted with ether. The extract was washed with water and a saturated aqueous solution of sodium chloride, successively, dried over anhydrous magnesium sulfate, and evaporated. The residue was purified by silica gel flash chromatography (n-hexane:ethyl acetate=1:1) to give the title compound (193 mg) having the following physical data.

NMR: δ7.40-7.00 (11H, m), 6.90-6.50 (3H, m), 5.26 (1H, s), 4.75 (2H, brs), 4.58 (2H, s), 3.78 (3H, s), 2.64 (2H, t, J=7Hz), 2.40 (2H, t, J=7Hz), 2.00 (2H, m); MS (m/z): 461 (M$^+$+1).

Reference Example 18

Methyl 3-(3-cyanopropyl)phenoxyacetate

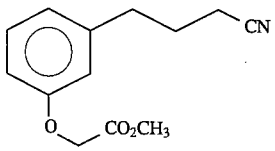

A mixture of potassium cyanide (1.16 g), 18-crown-6 (236 mg) and acetonitrile (18 ml) was stirred for 15 min under an atmosphere of argon. A mixture of methyl 3-(3-hydroxypropyl)phenoxyacetate (2.0 g) and tributylphosphine (1.99 g) in acetonitrile (10 ml) was added to the reaction mixture, followed by the dropwise addition of a solution of carbon tetrachloride (0.95 ml) in acetonitrile (10 ml) with cooling in ice bath. The mixture was stirred overnight at room temperature. The mixture was diluted with ether, and washed with aqueous 10% citric acid. After the addition of carbon tetrachloride (10 ml), the mixture was washed with water and a saturated aqueous solution of sodium chloride successively, dried over anhydrous magnesium sulfate, and evaporated. The residue was purified by silica gel column chromatography (ethyl acetate:n-hexane= 9:1) to give the title compound (1.47 g) having the following physical data.

NMR: δ7.20 (1H, t, J=7Hz), 6.90-6.60 (3H, m), 4.60 (2H, s), 3.80 ( 3H, s), 2.74 (2H, t, J=7Hz), 2.30(2H, t, J=7Hz), 1.98(2H, m).

Reference Example 19

Methyl 3-(4-amino-4-hydroxyiminobutyl)phenoxyacetate

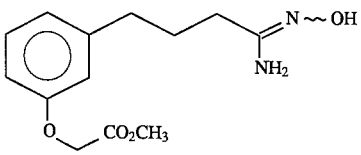

To a mixture of ethanol-water (5:1) (30 ml) were added successively the compound prepared in reference example 18 (1.01 g), hydroxyamine hydrochloride (331 mg) and sodium acetate (391 mg). The mixture was refluxed overnight. The mixture was concentrated under reduced pressure, and the residue was purified by silica gel column chromatography (n-hexane:ethyl acetate=1:1) to give the title compound (150 mg) having the following physical data.

NMR: δ7.13 (1H, t, J=7Hz), 6.90-6.50 (3H, m), 5.10 (3H, brs), 4.60 ( 2H, s), 3.80 (3H, s), 2.63 (2H, t, J=7Hz), 2.37 (2H, t, J=7Hz), 1.95 (2H, m).

Reference Example 20

Methyl 3-(4-amino-4-diphenylmethylcarbonyloxyiminobutyl)phenoxy acetate

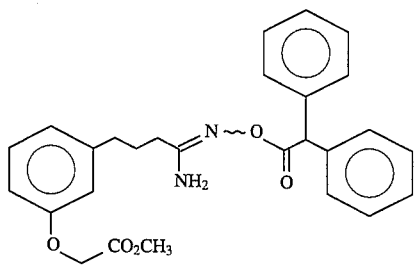

A suspension of diphenylacetic acid (252 mg) and thionyl chloride (5.0 ml) was refluxed for 1 h. The mixture was cooled to room temperature and concentrated under reduced pressure. To a solution of the residue and the compound prepared in reference example 19 (144 mg) in methylene chloride (5.0 ml) was added triethylamine (0.33 ml) at room temperature. The mixture was stirred overnight at room temperature quenched by addition of water, and extracted with ether. The extract was washed with water and a saturated aqueous solution of sodium chloride, successively, dried over anhydrous magnesium sulfate and evaporated. The residue was purified by silica gel flash chromatography (n-hexane:ethyl acetate=1:1) to give the title compound (61 mg) having the following physical data.

NMR: δ7.40-7.00 (11H, m), 6.90-6.50 (3H, m), 5.10 (1H, s), 4.58 (2H, s), 3.79 (3H, s), 2.60 (2H, m), 2.21 (2H, m), 1.90 (2H, m); MS (m/z): 461 (M$^+$+1).

Reference Example 21

1-(5,5-Dibromo-4-pentenyl)-3-methoxybenzene

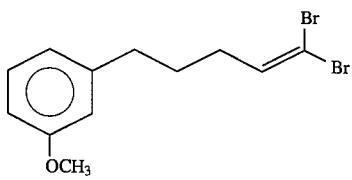

To a solution of carbon tetrabromide (16.7 g) in methylene chloride (35 ml) was added triphenylphosphine (26.0 g) in methylene chloride (35 ml) at 0° C., and the mixture was stirred for 10 min. To the mixture was added a solution of 1-(3-formylpropyl)-3-methoxybenzene (3.00 g) in methylene chloride (20 ml) at 0° C. The mixture was stirred for 30 min at 0° C. To the mixture was added gradually n-hexane and to remove triphenylphosphineoxide. The mixture was filtered was washed with water and a saturated aqueous solution of sodium chloride, successively, dried over anhydrous magnesium sulfate and evaporated. The residue was purified by silica gel column chromatography (n-hexane:ethyl acetate=24:1) to give the title compound (5.33 g) having the following physical data.

MS (m/z): 334 (M⁺). TLC: Rf 0.34 (n-hexane:ethyl acetate=24:1).

Reference Example 22

1-(4-pentynyl)-3-methoxybenzene

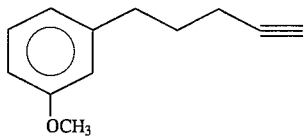

To a solution of the compound prepared in reference example 21 (3.58 g) in THF (40 ml) was added dropwise n-butyllithium (14.7 ml; 1.6 M/L in hexane solution) at −70° C. The mixture was stirred for 30 min at −70° C. After quenched by addition of water and aqueous solution of ammonium chloride at the same temperature, the mixture was warmed up to room temperature. The mixture was extracted with n-hexane - ethyl acetate (6:1). The extract was washed with water and a saturated aqueous solution of sodium chloride successively, dried over anhydrous magnesium sulfate, and evaporated. The residue was purified by silica gel column chromatography (n-hexane:ethyl acetate= 24:1) to give the title compound (1.86 g) having the following physical data.

TLC: Rf 0.32 (n-hexane:ethyl acetate=24:1); IR(cm⁻¹): v3295, 2943, 2117, 1602, 1489, 1261.

Reference Example 23

1-(7,7-Diphenyl-6-oxo-4-heptynyl)-3-methoxybenzene

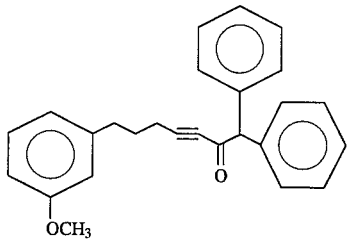

To a mixture of ethylmagnesium bromide (3.4 ml; 3.0 M/L in ether solution) and THF (20 ml) was added dropwise a solution of the compound prepared in reference example 22 (1.5 g) in THF (15 ml) over a 10 min period. The mixture was stirred for 2 h at room temperature. To the mixture was added a solution of diphenylacetaldehyde (1.7 g) in THF (10 ml). The mixture was stirred for 2 h. After quenched by addition of ammonium chloride, the mixture was extracted with ether. The extract was washed with water and a saturated aqueous solution of sodium chloride, successively, dried over anhydrous magnesium sulfate and evaporated. To a solution of the residue in ether (40 ml) was added manganese (IV) oxide (2.0 g) at room temperature. The mixture was stirred for 2 h. The mixture was filtrated, and evaporated. The residue was purified by silica gel column chromatography (n-hexane:ethyl acetate=7:1) to give the title compound (1.99 g) having the following physical data.

MS (m/z): 368 (M⁺). TLC: Rf 0.46 (n-hexane:ethyl acetate=3:1).

Reference Example 24

1-(6-Imino-4-hydroxy-7,7-diphenyl-4-heptynyl)-3-methoxybenzene

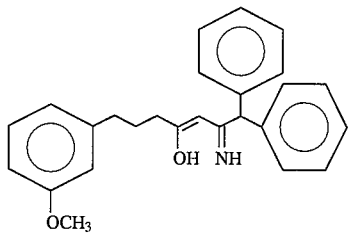

A mixture of the compound (400 mg) prepared by the same procedure as reference example 14 using the compound prepared in reference example 23, Raney nickel (300 mg; registered trade mark) and ethanol (5 ml) was stirred overnight under an atmosphere of hydrogen. The mixture was filtered through Celite (registered trade mark) and evaporated. The residue was purified by silica gel column chromatography (ethyl acetate:benzene=7:93) to give the title compound (184 mg) having the following physical data.

MS (m/z): 385 (M⁺). TLC: Rf 0.26 (n-hexane:ethyl acetate=3:1).

Reference Example 25

1-[3-(3-Diphenylmethylisothiazol-5-yl)propyl]-3-methoxybenzene

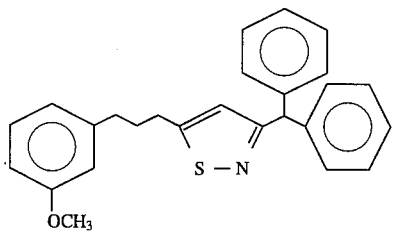

A mixture of the compound prepared in reference example 24 (121 mg), p-chloranil (77 mg), phosphorus pentasulfide (209 mg) and toluene (2 ml) was refluxed for 30 min. After cooled to room temperature to the mixture was added benzene. The mixture was filtrated, and evaporated. The residue was purified by silica gel column chromatography (n-hexane:ethyl acetate=6:1) to give the title compound (62 mg) having the following physical data.

MS (m/z): 399 (M⁺). TLC: Rf 0.30 (n-hexane:ethyl acetate=6:1).

Example 1

Methyl 3-(4-diphenylmethyloxyiminobutyl)phenoxyacetate

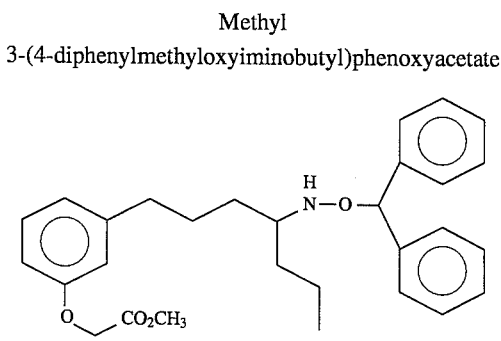

To a solution of the compound prepared in reference example 1 (300 mg) in ethanol (10 ml) was added diphenylmethyloxyamine (253 mg) at room temperature. The mixture was stirred overnight at room temperature and concentrated under reduced pressure. The residue was purified by silica gel column chromatography (benzene:ethyl acetate=9:1) to give the title compound (520 mg) having the following physical data.

TLC: Rf 0.31 (n-hexane:ethyl acetate=4:1); NMR: δ7.60-7.10 (12H, m), 6.90-6.80 (3H, m), 6.22 (1H, s), 4.60 (2H, s), 3.79 (3H, s), 2.80-2.00 (4H, m), 1.80 (2H, m).

Example 2

3-(4-Diphenylmethyloxyiminobutyl)phenoxyacetic acid

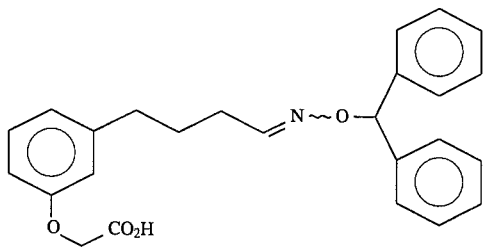

To a solution of the compound prepared in example 1 (305 mg) in a mixture of dimethoxymethane (3.0 ml) and methanol (1.0 ml) was added 2N aqueous solution of sodium hydroxide (0.5 ml) at room temperature. After being stirred for 1 h the mixture was quenched by addition of 1N hydrochloric acid (0.5 ml), and extracted with ethyl acetate. The extract was washed with water and a saturated aqueous solution of sodium chloride, successively, dried over anhydrous magnesium sulfate, and evaporated. The residue was purified by silica gel column chromatography (ethyl acetate:n-hexane=1:1) to give the title compound (277 mg) having the following physical data.

MS (m/z): 403 (M⁺), 381, 359, 345, 236, 219, 184, 168; NMR: δ7.55 (1H, t, J=6Hz), 7.40-7.10 (11H, m), 6.90-6.80 (3H, m), 6.20 (1H, s), 4.62 (2H, s), 2.80-2.40 (3H, m), 2.17 (1H, brs), 1.80 (2H, m).

Example 2(a)–2(c)

By the same procedure as in example 2, using the compound prepared in the same procedure as in reference example 1→example 1 which was using corresponding phenoxyacetic acid derivative compounds instead of methyl 3-(4-hydroxybutyl) phenoxyacetate, compounds having the following physical data shown in the table 3 were given.

TABLE 3

| EX. No. | Structure of the example compound | MS (m/z) | IR (cm⁻¹) |
|---|---|---|---|
| 2(a) | | 389(M⁺), 344, 222, 205, 184, 168 | [KBr method] ν 3030, 2911, 1743, 1708, 1610, 1515, 1455, 1431, 1237, 1189, 1095, 1023, 919, 832, 746, 705 |
| 2(b) | | 403(M⁺), 360, 345, 236, 219, 184, 118, 152 | ν 3030, 2927, 1736, 1611, 1586, 1510, 1454, 1301, 1218, 1180, 1081, 1022, 920, 830, 740, 702, 609 |

TABLE 3-continued

| EX. No. | Structure of the example compound | MS (m/z) | IR$_{(cm^{-1})}$ |
|---|---|---|---|
| 2(c) | | 390 (M$^+$ + 1) | v 3031, 2922, 1734, 1586, 1494, 1454, 1241, 1160, 1084, 1020, 919, 746, 700 |

The example compounds shown in table 3 are named as follows:

2(a) 4-(3-Diphenylmethyloxyiminopropyl)phenoxyacetic acid,
2(b) 4-(4-Diphenylmethyloxyiminobutyl)phenoxyacetic acid and
2(c) 3-(3-Diphenylmethyloxyiminopropyl)phenoxyacetic acid.

Example 3

Methyl 3-(4-diphenylmethyloxyiminoheptyl)phenoxyacetate

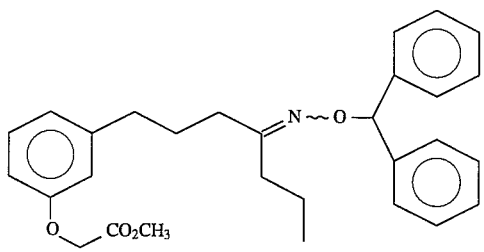

By the same procedure as in example 1, using the compound prepared in reference example 3, the title compound having the following physical data was given.

TLC: Rf 0.35 (n-hexane:ethyl acetate=3:1); IR (cm$^{-1}$): v3062, 3030, 2958, 2872, 1763, 1741, 1586, 1494, 1452, 1377, 1289, 1209, 1159, 1088, 1025, 937, 744, 700.

Example 4

3-(4-Diphenylmethyloxyiminoheptyl)phenoxyacetic acid

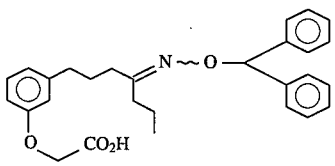

By the same procedure as in example 2, using the compound prepared in example 3, the title compound having the following physical data was given.

TLC: Rf 0.20 (chloroform:methanol=4:1); IR (cm$^{-1}$): v3031, 2961, 2872, 1737, 1587, 1494, 1454, 1375, 1241, 1160, 1086, 1042, 938, 763, 744, 700.

Example 5

Methyl 3-(4-diphenylmethyloxyaminoheptyl)phenoxyacetate

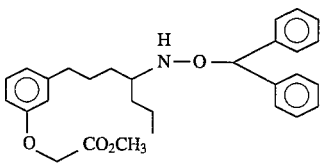

To solution of the compound prepared in example 3 (150 mg) in methanol (1 ml) was added sodium cyanoborohydride (82 mg) at room temperature. The solution was adjusted to pH 3 by addition of a saturated hydrochloride in methanol and this mixture was stirred for 2 h at room temperature. After being neutralized by addition of a saturated aqueous solution of sodium bicarbonate, the mixture was extracted with ethyl acetate. The extract was washed with water and aqueous solution of sodium chloride, successively, dried over anhydrous magnesium sulfate and evaporated. The residue was purified by silica gel column chromatography (n-hexane:ethyl acetate=3:1) to give title compound (147 mg) having the following physical data.

TLC: Rf 0.34 (n-hexane:ethyl acetate=3:1); IR (cm$^{-1}$): v3030, 2932, 2869, 1764, 1741, 1586, 1493, 1452, 1376, 1209, 1159, 1086, 1029, 888, 761, 743, 699.

Example 6

3-(4-Diphenylmethyloxyaminoheptyl)phenoxyacetic acid

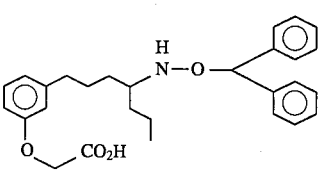

By the same procedure as example 2, using the compound prepared in example 5 (125 mg), the title compound (115 mg) having the following physical data was given.

TLC: Rf 0.21 (chloroform:methanol=4:1); IR (cm$^{-1}$): v3031, 2932, 2871, 1738, 1586, 1494, 1454, 1374, 1241, 1159, 1082, 1046, 915, 762, 744, 698.

Example 7

Methyl 3-(3,3-diphenylmethylpropyl)aminocarbonylmethyl)phenoxy acetate

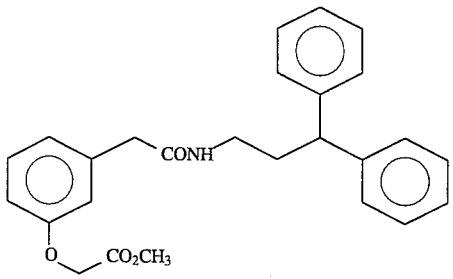

A mixture of 3-methoxycarbonylmethoxyphenylacetic acid (150 mg), 2-chloro-N-methylpyridinium iodide (241 mg), 3,3-diphenylpropylamine (146 mg) and triethylamine (0.26 ml) in methylene chloride (7 ml) was stirred overnight at room temperature. The mixture was poured into 1N hydrochloric acid, and extracted with ether. The extract was washed with water and a saturated aqueous solution of sodium chloride, successively, dried over anhydrous magnesium sulfate and evaporated. The residue was purified by silica gel column chromatography (ethyl acetate:methylene chloride=1:25) to give title compound (125 mg) having the following physical data.

TLC: Rf 0.33 (ethyl acetate:methylene chloride=1:9); NMR: δ7.40-7.00 (11H, m), 6.90-6.70 (3H, m), 5.30 (1H, m), 4.63 (2H, s), 3.83 (1H, t, J=7Hz), 3.80 (3H, s), 3.47 (2H, s), 3.17 (2H, dt, J=8, 7Hz), 2.20 (2H, dt, J=5, 7Hz).

Example 8

3-(3,3-diphenylpropyl)aminocarbonylmethyl) phenoxyacetic acid

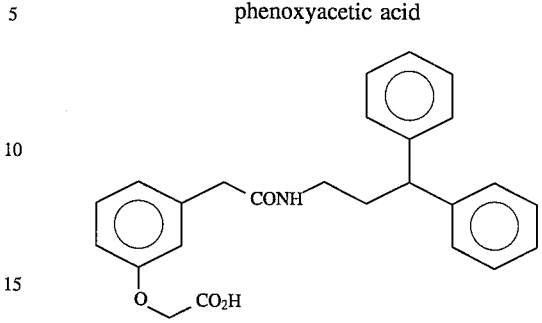

By the same procedure as example 2, using the compound prepared in example 7 (119 mg), the title compound (98 mg) having the following physical data was given.

TLC: Rf 0.48 (methylene chloride:methanol=10:3); IR (cm$^{-1}$): ν3295, 3024, 2880, 2526, 1757, 1584, 1557, 1490, 1469, 1450, 1381, 1356, 1304, 1285, 1242, 1204, 1155, 1087, 1030, 958, 905, 880, 776, 753, 741, 697, 674, 638, 614, 588, 557, 482, 456, 431.

Example 8(a)–8(cc)

By the same procedure as in example 7→example 2, using corresponding phenoxyacetic acid derivative compounds and corresponding amines, compounds having the following physical data shown in the table 4 were given.

TABLE 4

| EX. No. | Structure of the example compound | TLC | IR$_{(cm^{-1})}$ |
|---|---|---|---|
| 8(a) | | Rf 0.50 (methylene chloride:methanol = 10:3) | ν 3033, 1742, 1614, 1587, 1495, 1438, 1213, 1159, 1082, 1017, 780, 732, 702 |
| 8(b) | | Rf 0.53 (methylene chloride:methanol = 10:3) | ν 3436, 3031, 1742, 1603, 1494, 1452, 1363, 1221, 1160, 1083, 1029, 954, 775, 736, 700 |
| 8(c) | | Rf 0.30 (methylene chloride:methanol = 10:3) | [KBr method] ν 3268, 3057, 1724, 1636, 1588, 1561, 1492, 1453, 1432, 1400, 1368, 1348, 1314, 1283, 1259, 1231, 1172, 1158, 1093, 1080, 1026, 951, 919, 855, 787, 766, 744, 696, 618, 605, 557, 532, 489 |

TABLE 4-continued

| EX. No. | Structure of the example compound | TLC | IR $_{(cm^{-1})}$ |
|---|---|---|---|
| 8(d) | (3-CO₂H-CH₂-O-phenyl)-CH₂-CONH-CH(Ph)(Ph) | Rf 0.40 (methylene chloride:methanol = 10:3) | [KBr method] ν 3297, 3058, 2917, 1719, 1703, 1653, 1613, 1589, 1531, 1494, 1451, 1434, 1412, 1359, 1341, 1277, 1237, 1161, 1085, 1032, 978, 752, 742, 702, 642, 620 |
| 8(e) | (3-CO₂H-CH₂-O-phenyl)-CH₂-CONH-N(Ph)(Ph) | Rf 0.40 (methylene chloride:methanol = 10:3) | [KBr method] ν 3273, 3038, 2916, 1753, 1674, 1590, 1516, 1494, 1460, 1431, 1315, 1276, 1241, 1163, 1098, 1085, 1030, 965, 877, 784, 752, 693, 626, 546, 507 |
| 8(f) | (3-CO₂H-CH₂-O-phenyl)-CH₂-CONH-CH(Ph)(CH₂Ph) | Rf 0.40 (methylene chloride:methanol = 10:3) | [KBr method] ν 3318, 3063, 2921, 1752, 1646, 1586, 1540, 1495, 1440, 1255, 1165, 1100, 1028, 966, 914, 877, 760, 701, 541 |
| 8(g) | (3-CO₂H-CH₂-O-phenyl)-CH₂-CONH-CH₂-CH(Ph)(Ph) | Rf 0.40 (methylene chloride:methanol = 10:3) | [KBr method] ν 3309, 3028, 2912, 1724, 1625, 1604, 1580, 1494, 1435, 1299, 1246, 1160, 1087, 1013, 924, 886, 774, 756, 742, 704, 633, 585, 542 |
| 8(h) | (3-CO₂H-CH₂-O-phenyl)-CH₂-CONH-O-CH(Ph)(Ph) | Rf 0.38 (methylene chloride:methanol = 10:3) | [KBr method] ν 3233, 3032, 2912, 1719, 1641, 1609, 1588, 1532, 1494, 1458, 1436, 1341, 1300, 1250, 1161, 1098, 1086, 1054, 985, 914, 888, 813, 764, 748, 698, 602, 574, 531 |
| 8(i) | (3-CO₂H-CH₂-O-phenyl)-CH₂-CONH-N=C(Ph)(Ph) | Rf 0.40 (methylene chloride:methanol = 10:3) | [KBr method] ν 3314, 3057, 1737, 1639, 1587, 1511, 1490, 1446, 1367, 1324, 1304, 1221, 1158, 1075, 1028, 1000, 972, 918, 879, 774, 695, 651, 628, 549, 452 |

TABLE 4-continued

| EX. No. | Structure of the example compound | TLC | IR$_{(cm^{-1})}$ |
|---|---|---|---|
| 8(j) | (structure) | Rf 0.50 (methylene chloride:methanol = 10:3) | ν 3351, 3027, 2933, 1734, 1713, 1603, 1558, 1494, 1452, 1364, 1227, 1160, 1089, 1031, 914, 776, 752, 701 |
| 8(k) | (structure) | Rf 0.53 (methylene chloride:methanol = 10:3) | ν 3033, 2930, 1742, 1611, 1586, 1495, 1453, 1413, 1357, 1267, 1208, 1158, 1079, 1017, 878, 777, 700 |
| 8(l) | (structure) | Rf 0.53 (methylene chloride:methanol = 10:3) | ν 3031, 2927, 1746, 1604, 1495, 1452, 1361, 1223, 1160, 1083, 1029, 953, 879, 783, 735, 699 |
| 8(m) | (structure) | Rf 0.33 (methylene chloride:methanol = 10:3) | [KBr method] ν 3320, 3031, 2952, 2587, 1737, 1641, 1611, 1580, 1541, 1485, 1461, 1423, 1377, 1349, 1297, 1279, 1239, 1165, 1103, 1030, 1009, 925, 877, 781, 770, 735, 695 |
| 8(n) | (structure) | Rf 0.50 (methylene chloride:methanol = 10:3) | [KBr method] ν 3320, 3034, 2948, 1750, 1644, 1586, 1532, 1495, 1459, 1426, 1377, 1304, 1258, 1243, 1212, 1164, 1100, 1032, 935, 873, 756, 698, 644, 605 |
| 8(o) | (structure) | Rf 0.56 (methylene chloride:methanol = 10:3) | [KBr method] ν 3279, 3027, 2932, 2587, 1744, 1669, 1591, 1518, 1495, 1430, 1383, 1329, 1256, 1206, 1174, 1094, 1031, 939, 923, 853, 782, 746, 698, 631, 559 |

TABLE 4-continued

| EX. No. | Structure of the example compound | TLC | IR $_{(cm^{-1})}$ |
|---|---|---|---|
| 8(p) | (structure) | Rf 0.45 (methylene chloride:methanol = 10:3) | [KBr method] ν 3344, 3031, 2944, 1746, 1640, 1603, 1523, 1495, 1454, 1419, 1244, 1168, 1090, 1031, 902, 785, 781, 702, 642, 584, 538 |
| 8(q) | (structure) | Rf 0.47 (methylene chloride:methanol = 10:3) | [KBr method] ν 3347, 2938, 2866, 2549, 1737, 1615, 1587, 1553, 1493, 1452, 1437, 1362, 1293, 1226, 1158, 1083, 1028, 908, 877, 790, 758, 704, 630, 587, 543 |
| 8(r) | (structure) | Rf 0.44 (methylene chloride:methanol = 10:3) | [KBr method] ν 3205, 2930, 1736, 1655, 1586, 1494, 1452, 1229, 1160, 1082, 1023, 875, 762, 746, 698 |
| 8(s) | (structure) | Rf 0.50 (methylene chloride:methanol = 10:3) | [KBr method] ν 3482, 3159, 3053, 2965, 2905, 2759, 2524, 1746, 1637, 1584, 1489, 1457, 1432, 1397, 1359, 1322, 1309, 1272, 1229, 1156, 1087, 1028, 956, 927, 873, 774, 741, 695, 637, 600, 523, 463, 431 |
| 8(t) | (structure) | Rf 0.32 (methylene chloride:methanol = 10:3) | [KBr method] ν 3326, 3023, 2920, 2880, 1719, 1585, 1494, 1484, 1451, 1435, 1378, 1312, 1293, 1249, 1208, 1168, 1091, 894, 865, 785, 770, 750, 696, 606, 585, 495, 468 |
| 8(u) | (structure) | Rf 0.49 (methylene chloride:methanol = 10:3) | ν 3031, 2931, 1746, 1613, 1587, 1495, 1454, 1416, 1266, 1211, 1159, 1082, 1018, 883, 778, 756, 700 |

TABLE 4-continued
| EX. No. | Structure of the example compound | TLC | IR (cm$^{-1}$) |
|---|---|---|---|
| 8(v) | 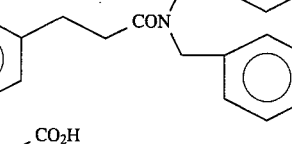 | Rf 0.53 (methylene chloride:methanol = 10:3) | ν 3030, 2927, 1746, 1603, 1494, 1452, 1361, 1217, 1161, 1082, 1029, 1002, 956, 883, 752, 699 |
| 8(w) | 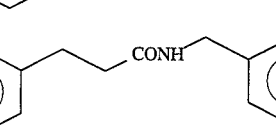 | Rf 0.21 (methylene chloride:methanol = 10:3) | [KBr method] ν 3347, 3293, 3033, 2935, 1742, 1712, 1640, 1610, 1587, 1547, 1492, 1454, 1432, 1350, 1301, 1281, 1213, 1159, 1104, 1080, 1020, 922, 887, 781, 749, 695, 498, 456 |
| 8(x) |  | Rf 0.43 (methylene chloride:methanol = 10:3) | [KBr method] ν 3326, 3061, 1752, 1651, 1614, 1585, 1535, 1496, 1455, 1427, 1381, 1299, 1246, 1220, 1166, 1106, 980, 922, 874, 799, 769, 745, 697, 640, 532 |
| 8(y) | 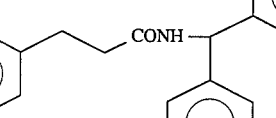 | Rf 0.40 (methylene chloride:methanol = 10:3) | [KBr method] ν 3279, 1737, 1704, 1673, 1589, 1523, 1496, 1453, 1414, 1301, 1280, 1234, 1160, 1086, 921, 771, 747, 693, 630, 507 |
| 8(z) |  | Rf 0.38 (methylene chloride:methanol = 10:3) | [KBr method] ν 3328, 3063, 3030, 2916, 2582, 1752, 1641, 1595, 1537, 1495, 1455, 1432, 1319, 1300, 1251, 1175, 1094, 1030, 913, 847, 790, 759, 699, 644, 539, 508 |
| 8(aa) | 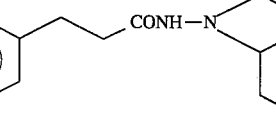 | Rf 0.50 (methylene chloride:methanol = 10:3) | [KBr method] ν 3339, 3060, 2931, 1737, 1603, 1561, 1494, 1452, 1224, 1159, 1087, 1032, 1008, 881, 783, 755, 742, 701, 586, 540 |

TABLE 4-continued

| EX. No. | Structure of the example compound | TLC | IR$_{(cm^{-1})}$ |
|---|---|---|---|
| 8(bb) | | Rf 0.33 (methylene chloride:methanol = 10:3) | [KBr method] ν 3209, 3032, 1736, 1656, 1494, 1452, 1229, 1161, 1084, 1002, 876, 762, 746, 699 |
| 8(cc) | | Rf 0.48 (methylene chloride:methanol = 10:3) | [KBr method] ν 3181, 3070, 3025, 2924, 2524, 1736, 1631, 1584, 1490, 1460, 1440, 1397, 1335, 1313, 1284, 1265, 1232, 1159, 1113, 1094, 1030, 958, 929, 912, 881, 783, 772, 736, 691, 637, 612, 597, 545, 470, 443 |

The example compounds shown in table 4 are named as follows:

8(a) 3-(N-Benzyl-N-phenylaminocarbonylmethyl)phenoxyacetic acid,
8(b) 3-(N,N-Dibenzylaminocarbonylmethyl)phenoxyacetic acid,
8(c) 3-(N-Benzylaminocarbonylmethyl)phenoxyacetic acid,
8(d) 3-(Diphenylmethylaminocarbonylmethyl)phenoxyacetic acid,
8(e) 3-[(N,N-Diphenylamino)aminocarbonylmethyl]phenoxyacetic acid,
8(f) 3-(1,2-Diphenylethylaminocarbonylmethyl)phenoxyacetic acid,
8(g) 3-(2,2-Diphenylethylaminocarbonylmethyl)phenoxyacetic acid,
8(h) 3-(Diphenylmethyloxyaminocarbonylmethyl)phenoxyacetic acid,
8(i) 3-[(1,1-Diphenylmethylideneamino)aminocarbonylmethyl]phenoxyacetic acid,
8(j) 3-[3-(3,3-Diphenylpropylaminocarbonyl)propyl]phenoxyacetic acid,
8(k) 3-[3-(N-Benzyl-N-phenylaminocarbonyl)propyl]phenoxyacetic acid,
8(l) 3-[3-(N,N-Dibenzylaminocarbonyl)propyl]phenoxyacetic acid,
8(m) 3-(3-Benzylaminocarbonylpropyl)phenoxyacetic acid,
8(n) 3-(3-Diphenylmethylaminocarbonylpropyl)phenoxyacetic acid,
8(o) 3-[3-[(N,N-Diphenylamino)aminocarbonyl]propyl]phenoxyacetic acid,
8(p) 3-[3-(1,2-Diphenylethylaminocarbonyl)propyl]phenoxyacetic acid,
8(q) 3-[3-(2,2-Diphenylethylaminocarbonyl)propyl]phenoxyacetic acid,
8(r) 3-(3-Diphenylmethyloxyaminocarbonylpropyl)phenoxyacetic acid,
8(s) 3-[3-[(1,1-Diphenylmethylideneamino)aminocarbonyl]propyl]phenoxy acetic acid,
8(t) 3-[2-(3,3-Diphenylpropylaminocarbonyl)ethyl]phenoxyacetic acid,
8(u) 3-[2-(N-Benzyl-N-phenylaminocarbonyl)ethyl]phenoxyacetic acid,
8(v) 3-[2-(N,N-Dibenzylaminocarbonyl)ethyl]phenoxyacetic acid,
8(w) 3-(2-Benzylaminocarbonylethyl)phenoxyacetic acid,
8(x) 3-(2-Diphenylmethylaminocarbonylethyl)phenoxyacetic acid,
8(y) 3-[2-[(N,N-Diphenylamino)aminocarbonyl]ethyl]phenoxyacetic acid,
8(z) 3-[2-(1,2-Diphenylethylaminocarbonyl)ethyl]phenoxyacetic acid,
8(aa) 3-[2-(2,2-Diphenylethylaminocarbonyl)ethyl]phenoxyacetic acid,
8(bb) 3-(2-Diphenylmethyloxyaminocarbonylethyl)phenoxyacetic acid,
8(cc) 3-[2-[(1,1-Diphenylmethylideneamino )aminocarbonyl]ethyl]phenoxy acetic acid.

Example 9

3-(4-Diphenylaminosulfonyl-3-butenyl)phenoxyacetic acid

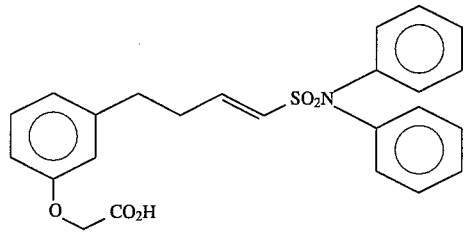

To a solution of the compound (0.08 g) prepared by the same procedure as in reference example 1, using the compound prepared in reference example 8, in acetone (2.0 ml) was added 8N Jone's reagent (0.1 ml) at 0° C. After stirring for 10 min at 0° C., to the mixture was added isopropyl alcohol (0.5 ml). The mixture was stirred for 10 min, water, and the mixture was with ether. The extract was washed with water and a saturated aqueous solution of sodium chloride, successively, dried over anhydrous magnesium sulfate, and evaporated. The residue was purified by silica gel column chromatography (methylene chloride→methylene chloride:methanol=40:1) to give the title compound (0.035 g) having the following physical data.

TLC: Rf 0.18 (methylene chloride:methanol=5:1); IR [KBr tablet method] (cm$^{-1}$): ν3435, 3051, 2928, 1749, 1714, 1611, 1586, 1489, 1452, 1424, 1353, 1262, 1224, 1193, 1164, 1147, 1091, 1027, 1011, 975, 912, 865, 824, 781, 757, 694, 631, 596, 547.

Example 10

3-(4-Diphenylaminosulfonylbutyl)phenoxyacetic acid

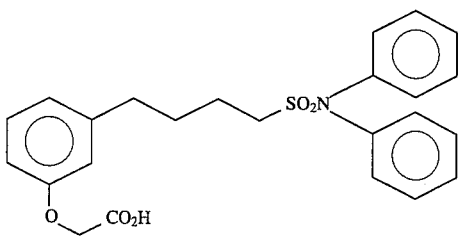

To a solution of the compound prepared in example 9 (410 mg) in ethyl acetate (5.0 ml) was added an excess amount of diazomethane in ether at 0° C. After 10 min, the mixture was evaporated. The residue was purified by silica gel column chromatography (n-hexane:ethyl acetate=2:1) to give a methyl ester compound (56 mg). To a solution of the methyl ester compound (56 mg) in methanol (5 ml) was added 10% palladium on activated carbon (50 mg) at room temperature. The mixture was stirred vigorously for 6 h under an atmosphere of hydrogen. The catalyst was removed by filtration through Celite. Evaporation of the solvent gave (54 mg) of the residue. By the same procedure as in example 2, using the residue, the title compound (36 mg) having physical data was given.

TLC: Rf 0.21 (methylene chloride:methanol=5:1); IR [KBr tablet method] (cm$^{-1}$): ν2925, 2862, 2590, 1750, 1710, 1612, 1586, 1488, 1463, 1451, 1424, 1350, 1302, 1287, 1258, 1243, 1218, 1197, 1164. 1146, 1103, 1078, 1027, 1012, 978, 913, 865, 780, 759, 708, 695, 626, 594, 534.

Example 11

Methyl 3-(4-diphenylmethyloxybutyl)phenoxyacetate

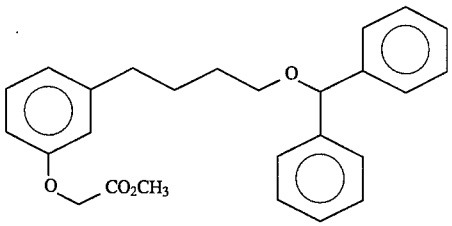

To a solution of methyl 3-(4-hydroxybutyl)phenoxyacetate (372 mg) and diphenylmethyltrichloroacetoimidate (771 mg) in chloroform (4 ml) and cyclohexane (8 ml) was added a catalytic amount of boron trifluoride etherate at 0° C. After being stirred for 30 min at 0° C., the mixture was quenched by addition of a saturated aqueous solution of sodium bicarbonate and extracted with ether. The extract was washed with water and a saturated aqueous solution of sodium chloride, successively, dried over anhydrous magnesium sulfate and evaporated. The residue was purified by silica gel column chromatography (n-hexane:ethyl acetate=4:1) to give the title compound (343 mg) having the following physical data.

NMR: δ7.50-7.00 (11H, m), 6.90-6.50 (3H, m), 5.27 (1H, s), 4.58 (2H, s). 3.77 (3H, s), 3.43 (2H, t, J=7Hz), 2.58 (2H, t, J=7Hz), 1.68 (4H, m); IR (cm$^{-1}$): ν3029, 2938, 2860, 1762, 1586, 1494, 1453, 1211, 1159, 1095, 1029, 743, 699.

Example 12

3-(4-Diphenylmethyloxybutyl)phenoxyacetic acid

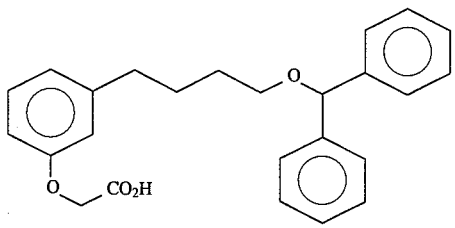

By the same procedure as in example 2, using the compound prepared in example 11 (340 mg), the title compound (277 mg) having the following physical data was given.

TLC: Rf 0.18 (chloroform:methanol=9:1); IR (cm$^{-1}$): ν3030, 2938, 2862, 1733, 1586, 1494, 1454, 1242, 1160, 1094, 761, 744, 699.

Example 12(a)

3-(3-Diphenylmethyloxypropyl)phenoxyacetic acid

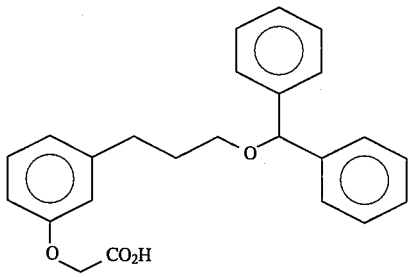

By the same procedure as in example 11→example 2, using methyl 3-(3-hydroxypropyl)phenoxyacetate instead of methyl 3-(4-hydroxybutyl) phenoxycacetate, the title compound having the following physical data was given.

mp.: 110°–112° C.; TLC: Rf 0.15 (ethyl acetate); IR [KBr tablet method] (cm$^{-1}$): ν2861, 1748, 1710, 1594, 1494, 1431, 1398, 1307, 1237, 1174, 1105, 1083, 1059, 1030, 904, 859, 783, 741, 697, 651, 612.

Example 13

Methyl 3-(4-triphenylmethoxybutyl)phenoxyacetate

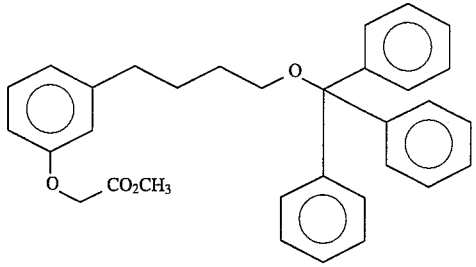

To a solution of methyl 3-(4-hydroxybutyl) phenoxyacetate (174 mg) in dimethylformamide (8.0 ml) was added successively trityl chloride (223 mg) and N,N-dimethylaminopyridine (88 mg). After stirred overnight at room temperature, the mixture was quenched by addition of water and extracted with ether. The extract was washed with water and a saturated aqueous solution of sodium chloride, successively dried over anhydrous magnesium sulfate, and evaporated. The residue was purified by flash silica gel chromatography (n-hexane:ethyl acetate=4:1) to give the title compound (228 mg) having the following physical data.

NMR: δ7.50–7.00 (16H, m), 6.90–6.50 (3H, m), 4.58 (2H, s), 3.78 (3H, s), 3.04 (2H, t, J=7Hz), 2.53 (2H, m), 1.66 (4H, m); IR ($cm^{-1}$): ν3057, 2938, 2865, 1764, 1741, 1586, 1490, 1449, 1289, 1211, 1158, 1075, 1033, 764, 707.

Example 14

3-(4-Triphenylmethoxybutyl)phenoxyacetic acid

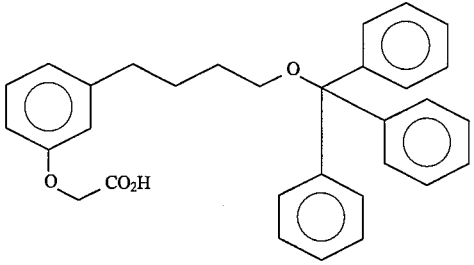

By the same procedure as in example 2, using the compound prepared in example 13 (220 mg), the title compound (159 mg) having the following physical data was given.

TLC: Rf 0.13 (chloroform:methanol=9:1); IR ($cm^{-1}$): ν 3058, 2937, 2866, 1738, 1586, 1490, 1449, 1240, 1159, 1075, 900, 764, 698.

Example 15

Methyl 3-(3-diphenylmethyloxycarbonylpropyl) phenoxyacetate

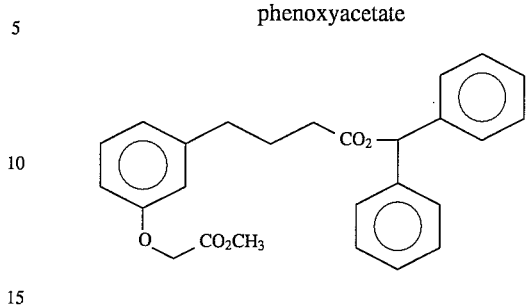

A mixture of 3-(3-methoxycarbonylmethoxyphenyl)propionic acid (195 mg), 2-chloro-N-methylpyridinium iodide (297 mg), diphenylmethanol (185 mg), triethylamine (0.32 ml), and catalytic amount of N,N-dimethyaminopyridine in methylene chloride (6 ml) was stirred overnight at room temperature. The mixture was poured into 1N hydrochloric acid extracted with ethyl acetate. The extract was washed with water and saturated aqueous solution of sodium chloride, successively, dried over anhydrous magnesium sulfate and evaporated. The residue was purified by silica gel column chromatography (n-hexane:ethyl acetate=4:1) to give the title compound (128 mg) having the following physical data.

TLC: Rf 0.54 (n-hexane:ethyl acetate=7:3); NMR: δ7.40–7.10 (11H, m), 6.89 (1H, s), 6.85–6.60 (3H, m), 4.60 (2H, s), 3.79 (3H, s), 2.60 (2H, t, J=6Hz), 2.43 (2H, t, J=7Hz), 1.97 (2H, m).

Example 16

Methyl 3-[3-(4-diphenylmethylpyrazol-1-yl)propyl]phenoxyacetate

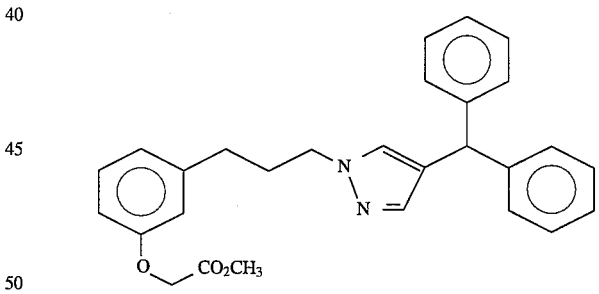

To a suspension of sodium hydride (217 mg, 60% dispersion) in dimethylformamide (10 ml) was added dropwise a solution of 4-diphenylmethylpyrazole (1.27 g) in dimethylformamide (50 ml) at room temperature. After being stirred for 30 min at room temperature, to the mixture was added dropwise a solution of the compound prepared in reference example 9(1.56 g) in dimethylformamide. After being stirred for 1 h, the mixture was quenched by addition of 1N hydrochloric acid and extracted with a mixture of ethyl acetate-n-hexane (1:2). The extract was washed with saturated aqueous solution of sodium chloride, dried over anhydrous magnesium sulfate and evaporated. The residue was purified by silica gel column chromatography (ethyl acetate:n-hexane=3:7) to give the title compound (2.01 g) having the following physical data.

TLC: Rf 0.59 (n-hexane:ethyl acetate=1:1); NMR: δ7.40-7.10 (12H, m), 6.93 (1H, s), 6.80-6.60 (3H, m), 5.35 (1H, s), 4.58 (2H, s), 4.03 (2H, t, J=7Hz), 3.79 (3H, s), 2.56 (2H, t, J=7Hz), 2.16 (2H, m).

Example 17

3-[3-(4-diphenylmethylpyrazol-1-yl)propyl]phenoxyacetic acid

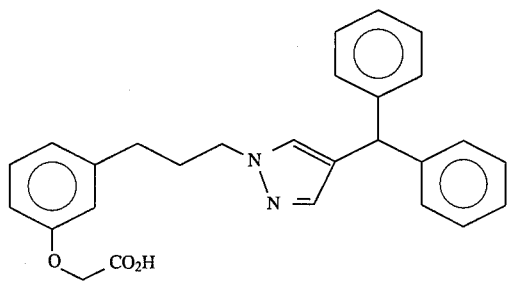

By the same procedure as in example 2, using the compound prepared in example 16 (1.5 g), the title compound (1.1 g) having the following physical data was given.

TLC: Rf 0.21 (chloroform:methanol=4:1); IR [KBr tablet method] (cm$^{-1}$): ν3027, 2930, 1736, 1586, 1493, 1451, 1219, 1159, 1079, 1014, 874, 753, 701, 507.

Example 17(a)–17(dd)

By the same procedure as in reference example 9→example 16→example 17, using corresponding compounds, compounds having the following physical data shown in the table 5 were given.

TABLE 5

| EX. No. | Structure of the example compound | TLC | IR$_{(cm^{-1})}$ |
|---|---|---|---|
| 17 (a) | | Rf 0.26 (chloroform: methanol = 4:1) | ν3027, 2936, 2861, 2517, 1736, 1586, 1494, 1451, 1374, 1219, 1158, 1079, 1015, 873, 753, 700, 635, 508, 475 |
| 17 (b) | | Rf 0.19 (chloroform: methanol = 4:1) | ν3029, 2932, 1737, 1587, 1494, 1452, 1373, 1242, 1160, 1080, 1032, 848, 780, 700 |
| 17 (c) | | Rf 0.15 (chloroform: methanol = 4:1) | ν3028, 2929, 1736, 1586, 1494, 1452, 1216, 1160, 1079, 878, 754, 699, 637 |

TABLE 5-continued
| Ex. No. | Structure | TLC (Rf) | NMR (δ) |
|---|---|---|---|
| 17 (d) | 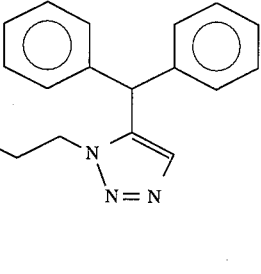 | Rf 0.14 (chloroform: methanol = 4:1) | v3029, 2929, 2508, 1736, 1586, 1493, 1454, 1222, 1160, 1114, 1081, 1032, 849, 751, 701, 639 |
| EX. No. | Structure of the example compound | TLC (Rf) | NMR (δ) |
|---|---|---|---|
| 17 (e) | 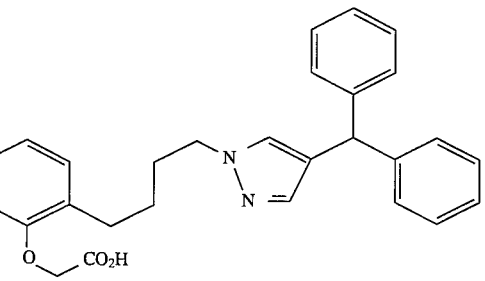 | 0.60 (methanol: methylene chloride = 1:4) | 7.30–7.00 (12H, m), 6.96 (1H, s), 6.90–6.80 (2H, m), 6.76 (1H, d), 5.30 (1H, s), 4.60 (2H, s), 4.10 (2H, t), 2.67 (2H, t), 1.83 (2H, m), 1.60 (2H, m). |
| 17 (f) | 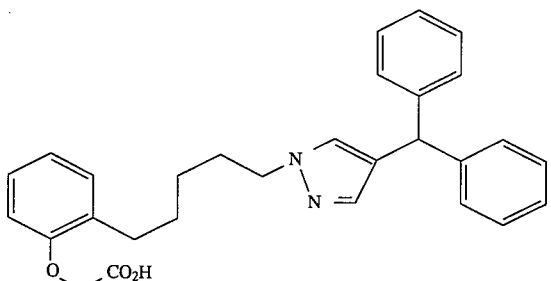 | 0.63 (methanol: methylene chloride = 1:4) | 7.50 (1H, brs), 7.35–7.00 (13H, m), 6.93 (1H, s), 6.90 (1H, t), 6.75 (1H, d), 5.30 (1H, s), 4.60 (2H, s), 4.05 (2H, t), 2.67 (2H, t), 1.85 (2H, m), 1.63 (2H, m), 1.30 (2H, m), |
| 17 (g) | 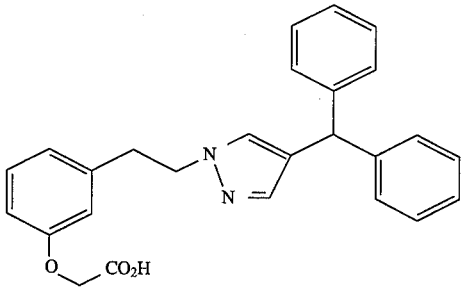 | 0.19 (methanol: methylene chloride = 1:5) | 7.4–7.0 (12H, m), 6.82 (2H, m), 6.72 (1H, s), 6.67 (1H, t), 6.0–4.8 (1H, brs), 5.28 (1H, s), 4.58 (2H, s), 4.29 (2H, t), 3.05 (2H, t) |
| 17 (h) | 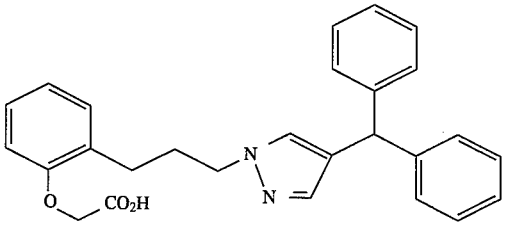 | 0.33 (methanol: methylene chloride = 1:5) | 8.0–7.2 (1H, brs), 7.4–7.0 (13H, m), 7.02 (1H, s), 6.92 (1H, t), 6.76 (1H, d), 5.32 (1H, s), 4.58 (2H, s), 4.08 (2H, t), 2.66 (2H, t), 2.17 (2H, tt) |

TABLE 5-continued

| | Structure | Rf | NMR |
|---|---|---|---|
| 17 (i) | 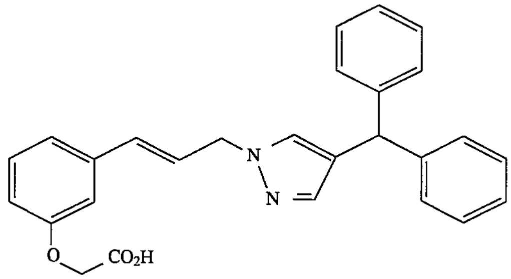 | 0.26 (chloroform: methanol = 4:1) | 7.95 (1H, brs), 7.36–7.13 (12H, m), 7.05 (1H, s), 6.96 (1H, d), 6.92 (1H, m), 6.78 (1H, dd), 6.48 (1H, d), 6.29 (1H, dt), 5.33 (1H, s), 4.82 (2H, d), 4.56 (2H, s). |
| 17 (j) | 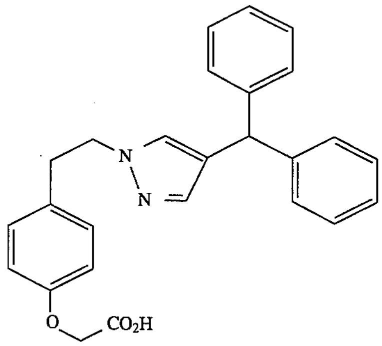 | 0.24 (methanol: methylene chloride = 1:5) | (CDCl3—CD3OD) 7.4–7.0 (11H, m), 6.94 (2H, d), 6.80 (2H, d), 6.72 (1H, s), 5.26 (1H, s), 4.56 (2H, s), 4.20 (2H, t), 3.03 (2H, t) |
| 17 (k) | 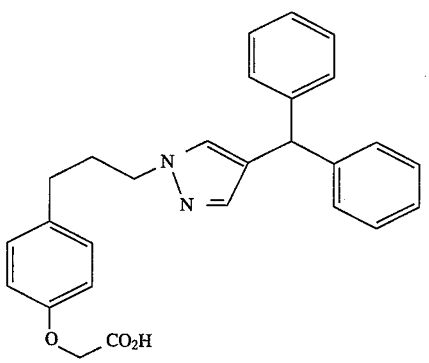 | 0.26 (methanol: methylene chloride = 1:5) | 7.5–7.1 (11H, m), 7.01 (2H, d), 6.95 (1H, s), 6.82 (2H, d), 5.34 (1H, s), 4.58 (2H, s), 4.07 (2H, t), 2.49 (2H, t), 2.08 (2H, tt) |
| 17 (l) | 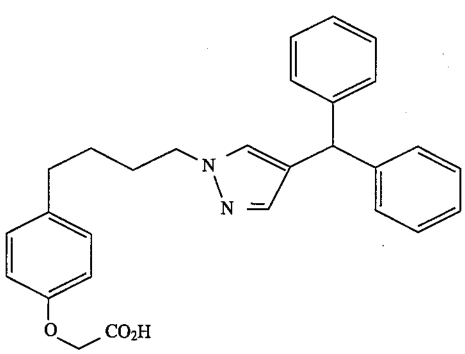 | 0.28 (methanol: methylene chloride = 1:5) | 7.5–7.1 (11H, m), 7.02 (2H, d), 6.96 (1H, s), 6.82 (2H, d), 6.6–5.6 (1H, brs), 5.33 (1H, s), 4.59 (2H, s), 4.07 (2H, t), 2.52 (2H, t), 1.82 (2H, m), 1.51 (2H, m). |
| 17 (m) | 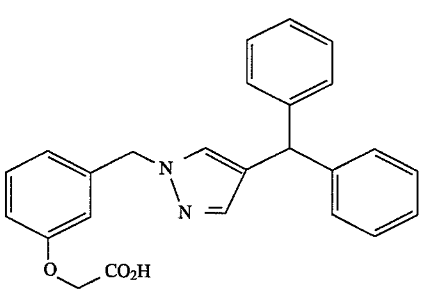 | 0.17 (methanol: methylene chloride = 1:5) | 7.4–7.3 (12H, m), 7.05 (1H, s), 6.9–6.7 (3H, m), 5.32 (1H, s), 5.20 (2H, s), 4.58 (2H, s). |

TABLE 5-continued

| | Structure | Rf (solvent) | NMR |
|---|---|---|---|
| 17 (n) | 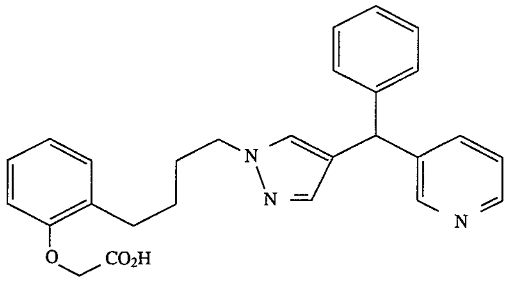 | 0.31 (chloroform: methanol = 4:1) | 8.70–8.00 (3H, m), 7.75–7.50 (1H, m), 7.35–6.97 (9H, m), 6.94–6.70 (3H, m), 5.43 (1H, brs), 5.60 (2H, brs), 4.08 (2H, m), 2.72 (2H, m), 2.06–1.50 (4H, m). |
| 17 (o) | 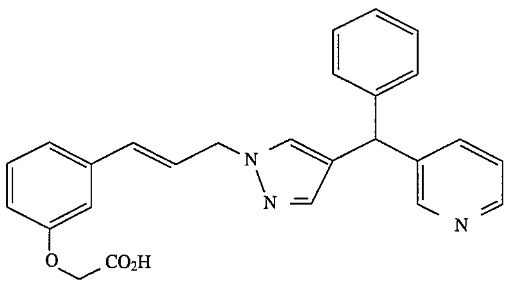 | 0.16 (methanol: methylene chloride = 1:5) | 8.47 (2H, m), 7.61 (1H, d), 7.40–7.13 (8H, m), 7.09 (1H, s), 7.00–6.80 (3H, m), 6.43 (1H, d), 6.27 (1H, dt), 5.42 (1H, s), 4.87 (2H, d), 4.62 (2H, s). |
| 17 (p) | 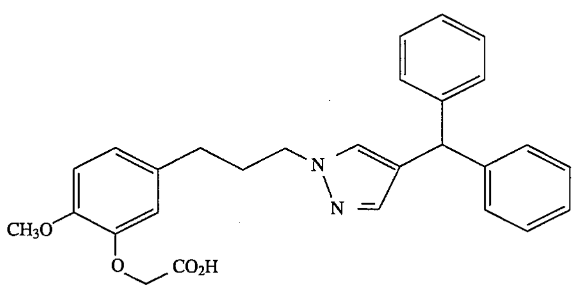 | 0.29 (chloroform: methanol = 4:1) | 7.36–7.13 (11H, m), 6.95 (1H, s), 6.94–6.70 (4H, m), 5.33 (1H, s), 4.75 (2H, s), 4.03 (2H, t), 3.84 (3H, s), 2.50 (2H, t), 2.20–2.02 (2H, m). |
| 17 (q) | 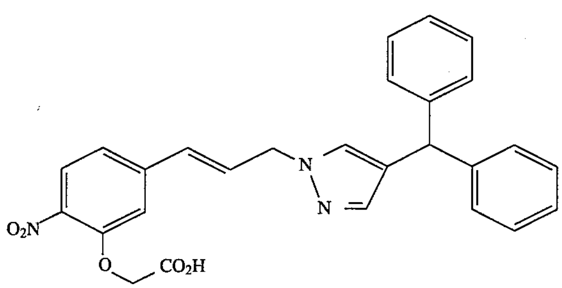 | 0.28 (methanol: methylene chloride = 1:5) | 7.83 (1H, d), 7.4–7.1 (11H, m), 7.07 (1H, s), 7.00 (1H, dd), 6.97 (1H d), 6.6–5.8 (1H, brs), 6.43 (2H, m), 5.35 (1H, s), 4.87 (2H, m), 4.75 (2H, s). |
| 17 (r) | 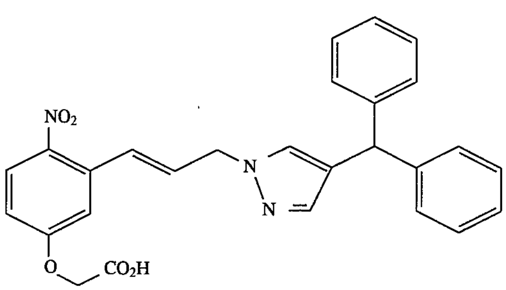 | 0.22 (methanol: methylene chloride = 1:5) | 8.02 (1H, d), 7.40 (1H, s), 7.4–7.1 (11H, m), 7.07 (1H, d,), 7.03 (1H, d), 6.88 (1H, dd), 6.32 (1H, dt) 6.2–5.2 (1H, brs), 5.36 (1H, s), 4.90 (2H, d), 4.68 (2H, s). |

TABLE 5-continued

| | Structure | Rf | NMR |
|---|---|---|---|
| 17 (s) | 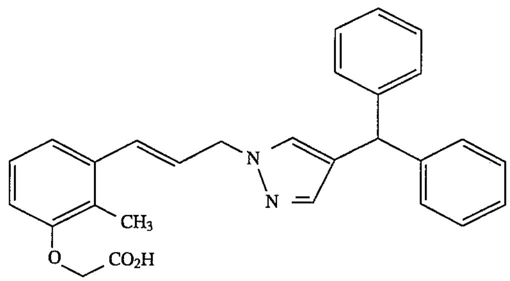 | 0.32 (chloroform: methanol = 4:1) | 7.38–6.98 (14H, m), 6.75 (1H, d), 6.65 (1H, t), 6.17 (1H, dt), 5.44 (1H, brs), 5.36 (1H, s), 4.88 (2H, d), 4.57 (2H, s), 2.20 (3H, s). |
| 17 (t) | 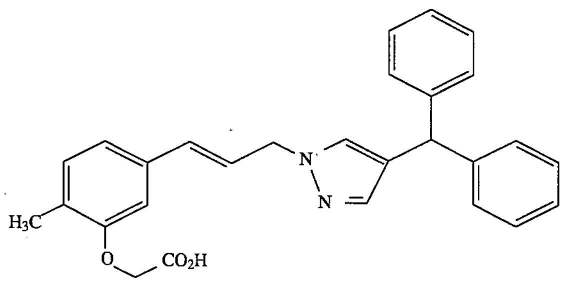 | 0.38 (chloroform: methanol = 4:1) | 7.38–7.00 (13H, m), 7.00–6.60 (1H, brs), 6.86 (1H, d), 6.74 (1H, s), 6.47 (1H, d), 6.24 (1H, dt), 5.32 (1H, s), 4.79 (2H, d), 4.62 (2H, s), 2.24 (3H, s). |
| 17 (u) | 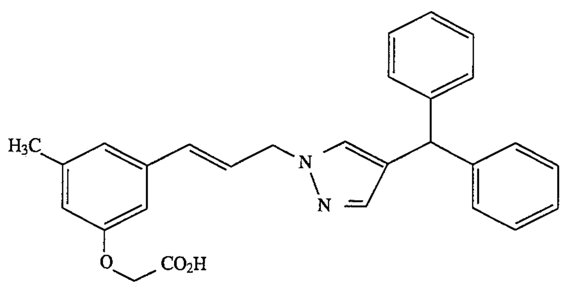 | 0.32 (chloroform: methanol = 4:1) | 7.38–7.00 (12H, m), 7.00–6.20 (1H, brs), 6.78 (1H, s), 6.70 (1H, s), 6.63 (1H, s), 6.43 (1H, d), 6.26 (1H, dt), 5.33 (1H, s), 4.81 (2H, d), 4.56 (2H, s), 2.26 (3H, s). |
| 17 (v) | 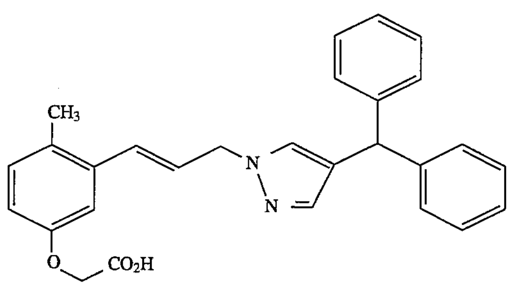 | 0.31 (chloroform: methanol = 4:1) | 7.40–6.90 (14H, m), 6.74 (1H, dd), 6.63 (1H, d), 6.40 (1H, brs), 6.20 (1H, dt), 5.35 (1H, s), 4.85 (2H, d), 4.57 (2H, s), 2.20 (3H, s). |
| 17 (w) | 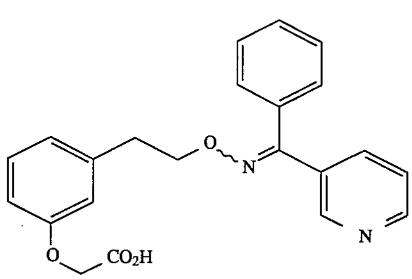 | 0.40 (methanol: methylene chloride = 1:4) | 8.63 and 8.47 (1H, s), 8.56 and 8.53 (1H, d), 7.78–7.73 and 7.62–7.37-(1H, m), 7.45–7.22 (6H, m), 7.16–7.09 (1H, m), 6.79–6.65 (3H, m), 4.43 (2H, s), 4.38–4.33 (2H, m), 2.96–2.88 (2H, m) |
| 17 (x) | 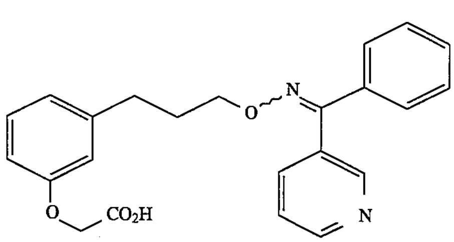 | 0.49 (methanol: methylene chloride = 1:4) | 8.71 and 8.62 (1H, s), 8.61 and 8.55 (1H, d), 7.80–7.76 and 7.70–7.67 (1H, m), 7.50–7.25 (6H, m), 7.13–7.06 (1H, m), 6.75–6.65 (3H, m), 4.45 (2H, s), 4.20–4.10 (2H, m), 2.60–2.50 (2H, m), 2.01–1.92 (2H, m) |

TABLE 5-continued

| | | | |
|---|---|---|---|
| 17 (y) | | 0.46 (methanol: methylene chloride = 1:4) | 8.81 and 8.67 (1H, s), 8.57 and 8.52 (1H, d), 7.73–7.65 (1H, m), 7.50–7.20 (6H, m), 7.10–7.05 (2H, m), 6.85 (1H, t), 6.73 (1H, d), 4.51 and 4.48 (2H, s), 4.25–4.18 (2H, m), 2.75–2.65 (2H, m), 2.10–1.98 (2H, m) |
| 17 (z) | | 0.46 (methanol: methylene chloride = 1:4) | 8.71 and 8.62 (1H, s), 8.55 and 8.52 (1H, d), 7.78–7.74 and 7.70–7.66 (1H, m), 7.47–7.15 (6H, m), 7.13–7.08 (2H, m), 6.88 (1H, t), 6.74 (1H, d), 4.54 (2H, s), 4.25–4.18 (2H, m), 2.73–2.65 (2H, m), 1.80–1.60 (4H, m). |
| 17 (aa) | | 0.43 (methanol: methylene chloride = 1:4) | 8.72 and 8.64 (1H, s), 8.59–8.50 (1H, m), 7.78–7.73 and 7.68–7.65 (1H, m), 7.46–7.15 (6H, m), 7.14–7.07 (2H, m), 6.90–6.85 (1H, m), 6.78–6.73 (1H, m), 4.52 (2H, s), 4.18 (2H, t), 2.67(2H, t), 1.80–1.69 (2H, m), 1.69–1.56 (2H, m), 1.44–1.34 (2H, m) |
| 17 (bb) | | 0.22 (methanol: methylene chloride = 1:5) | 8.80 (0.4H, d), 8.70 (0.6H, d), 8.67 (0.6H, dd), 8.62 (0.4H, dd), 7.87–7.72 (1H, m), 7.60–6.90 (9H, m), 6.90–6.78 (1H, m), 6.63 (0.4H, d), 6.55 (0.6H, d), 6.37 (0.6H, dt), 6.30 (0.4H, dt), 4.92–4.77 (2H, m), 4.67 (0.8H, s), 4.65 (1.2H, s). |
| 17 (cc) | | 0.19 (methanol: methylene chloride = 1:5) | 7.4–7.0 (12H, m), 6.8–6.0 (5H, m), 5.32 (1H, s), 4.58 (2H, s), 4.44 (2H, t), 4.24 (2H, t) |
| 17 (dd) | | 0.43 (methanol: methylene chloride = 1:4) | 8.67 and 8.57 (1H, s), 8.56 and 8.53 (1H, d), 7.77–7.73 and 7.70–7.65 (1H, m), 7.45–7.25 (6H, m), 7.13–7.06 (1H, m), 6.55–6.45 (3H, m), 4.55–4.40 (4H, m), 4.25–4.15 (2H, m) |

The example compounds shown in table 5 are named as follows:

17(a) 3-[4-(4-Diphenylmethylpyrazol-1-yl)butyl]phenoxy-acetic acid,

17(b) 3-[3-(4-Diphenylmethyl-1,2,3-triazol-2-yl)propyl]phenoxyacetic acid,

17(c) 3-[3-(4-Diphenylmethyl-1,2,3-triazol-1-yl)propyl]phenoxyacetic acid,

17(d) 3-[3-(4-Diphenylmethyl-1,2,3-triazol-3-yl)propyl]phenoxyacetic acid,

17(e) 2-[4-(4-Diphenylmethylpyrazol-1-yl)butyl]phenoxyacetic acid,

17(f) 2-[5-(4-Diphenylmethylpyrazol-1-yl)pentyl]phenoxyacetic acid,

17(g) 3-[2-(4-Diphenylmethylpyrazol-1-yl)ethyl]phenoxyacetic acid,

17(h) 2-[3-(4-Diphenylmethylpyrazol-1-yl)propyl]phenoxyacetic acid,

17(i) 3-[3-(4-Diphenylmethylpyrazol-1-yl)-1-propenyl]phenoxyacetic acid,

17(j) 4-[2-(4-Diphenylmethylpyrazol-1-yl)ethyl]phenoxyacetic acid,

17(k) 4-[3-(4-Diphenylmethylpyrazol-1-yl)propyl]phenoxyacetic acid,

17(l) 4-[4-(4-Diphenylmethylpyrazol-1-yl)butyl]phenoxyacetic acid,

17(m) 3-[(4-Diphenylmethylpyrazol-1-yl)methyl]phenoxyacetic acid,

17(n) 2-[4-(4-Diphenylmethylpyrazol-1-yl)butyl]phenoxyacetic acid,

17(o) 3-[3-[4-[1-Phenyl-1-(3-pyridyl)methyl]pyrazol-1-yl]-1-propenyl]phenoxy acetic acid, 17(p) 2-Methoxy-5-[3(4-diphenylmethylpyrazol-1-yl)propyl]phenoxyacetic acid, 17(q) 2-Nitro-5-[3-(4-diphenylmethylpyrazol-1-yl)-1-propenyl]phenoxyacetic acid, 17(r) 4-Nitro-3-[3-(4-diphenylmethylpyrazol-1-yl)-1-propenyl]phenoxyacetic acid, 17(s) 2-Methyl-3-[3-(4-diphenylmethylpyrazol-1-yl)-1-propenyl]phenoxyacetic acid, 17(t) 2-Methyl-5-[3-(4-diphenylmethylpyrazol-1-yl)-1-propenyl]phenoxyacetic acid, 17 (u) 3-Methyl-5-[3-(4-diphenylmethylpyrazol-1-yl)-1-propenyl]phenoxyacetic acid, 17 (v) 4-Methyl-3-[3-(4-diphenylmethylpyrazol-1-yl)-1-propenyl]phenoxyacetic acid, 17(w) 3-[2-[1-Phenyl-1-(3-pyridyl)methylideneaminooxy]ethyl]phenoxyacetic acid, 17(x) 3-[3-[1-Phenyl-1-(3-pyridyl)methylideneaminooxy]propyl]phenoxyacetic acid, 17(y) 2-[3-[1-Phenyl-1-(3-pyridyl)methylideneaminooxy]propyl]phenoxyacetic acid, 17(z) 2-[4-[1-Phenyl-1-(3-pyridyl)methylideneaminooxy]butyl]phenoxyacetic acid, 17(aa) 2-[5-[1-Phenyl-1-(3-pyridyl)methylideneaminooxy]pentyl]phenoxy acetic acid, 17(bb) 3-[3-[1-Phenyl-1-(3-pyridyl)methylideneaminooxy]-1-propenyl]phenoxy acetic acid, 17(cc) 3-[2-(4-Diphenylmethylpyrazol-1-yl)ethyloxy]phenoxyacetic acid 17(dd) 3-[2-[1-Phenyl-1-(3-pyridyl)methylideneaminooxy]ethyloxy]phenoxy acetic acid.

Example 18

Methyl 3-[3-(5-diphenylmethylisoxazol-3-yl)propyl]phenoxyacetate

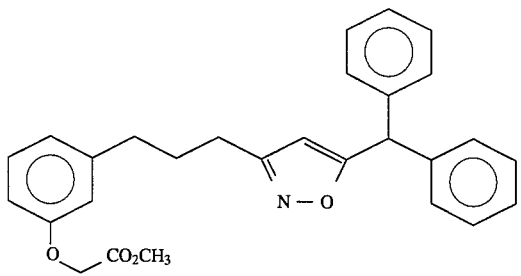

To a suspension of the compound prepared in reference example 16 (300 mg), potassium bicarbonate (138 mg) in dimethylformamide (4.0 ml) was added dropwise and methyl bromoacetate (0.095 ml) was added with stirring at room temperature. The mixture was stirred for 5 h at 50° C. The mixture was poured into water and extracted with ethyl acetate. The extract was washed with water and saturated aqueous solution of sodium chloride, successively, dried over anhydrous magnesium sulfate and evaporated. The residue was purified by silica gel column chromatography (benzene:ethyl acetate=19:1) to give the title compound (350 mg) having the following physical data.

TLC: Rf 0.22 (ethyl acetate:n-hexane=1:3); NMR: δ7.37-7.02 (11H, m), 6.85-6.67 (3H, m), 5.72 (1H, s), 5.51 (1H, s), 4.62 (2H, s), 3.79 (3H, s), 2.72-2.57 (4H, m), 2.05-1.86 (2H, m).

Example 19

3-[3-(5-diphenylmethylisoxazol-3-yl)propyl]phenoxyacetic acid

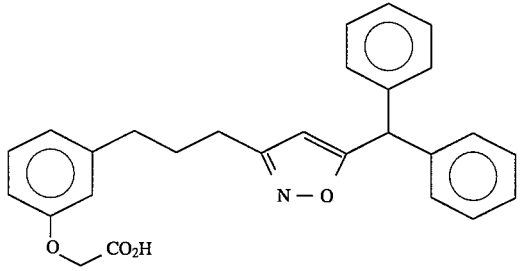

To a solution of the compound prepared in example 18 (295 mg) in tetrahydrofuran (2.0 ml) and methanol (1.0 ml) was added dropwise 1N aqueous solution of sodium hydroxide (1.0 ml) with stirring at room temperature. After being stirred for 30 min at room temperature. The mixture was neutralized by addition of 1N hydrochloric acid and was extracted with ethyl acetate. The extract was washed with water and a saturated aqueous solution of sodium chloride, successively, dried over anhydrous magnesium sulfate, and evaporated. The residue was purified by silica gel column chromatography (chloroform:methanol=49:1→9:1) to give the title compound (208 mg) having the following physical data.

TLC: Rf 0.25 (chloroform:methanol=4:1); IR [KBr tablet method] (cm$^{-1}$): v3401, 3028, 2924, 1796, 1494, 1452, 1425, 1340, 1248, 1160, 1078, 900, 791, 752, 699.

Example 19(a)–19(b)

By the same procedure as in reference example 14→reference example 16→example 18→example 19, using the compound prepared in reference example 23 and by the same procedure as in reference example 16→example 18→example 19, using the compound prepared in reference example 25, compounds having the following physical data shown in the table 6 were given.

NMR: δ7.40-7.10 (11H, m), 6.90 (1H, d, J=7Hz), 6.75 (1H, s), 6.72 (1H, d, J=7Hz), 5.58(1H, s), 4.60 (2H, s), 3.79 (3H, s), 2.87 (2H, t, J=7Hz), 2.67 (2H, t, J=7Hz), 2.11 (2H,m); MS(m/z): 442 (M$^+$), 250, 167.

TABLE 6

| EX. No. | Structure of the example compound | TLC (Rf) | NMR (δ) |
|---|---|---|---|
| 19 (a) | | 0.14 (chloroform: methanol = 9:1) | 7.4–6.5 (1H, brs), 7.38–7.14 (11H, m), 6.82 (1H, d), 6.77–6.72 (2H, m), 5.81 (1H, s), 5.55 (1H, s), 4.65 (2H, s), 2.71 (2H, t), 2.65 (2H, t), 2.09–1.92 (2H, m). |
| 19 (b) | | 0.19 (chloroform: methanol = 17:3) | 7.35–7.12 (11H, m), 6.84–6.69 (4H, m), 5.97 (1H, brs), 5.66 (1H, s), 4.64 (2H, s), 2.85 (2H, t), 2.64 (2H, t), 2.08–1.90 (2H, m). |

The example compounds shown in table 6 are named as follows:

19(a) 3-[3-(3-Diphenylmethylisoxazol-5-yl)propyl]phenoxyacetic acid and
19(b) 3-[3-(3-Diphenylmethylisothiazol-5-yl)propyl]phenoxyacetic acid.

Example 20

Methyl 3-[3-(3-diphenylmethyl-1,2,4-oxadiazol-5-yl)propyl]phenoxy acetate

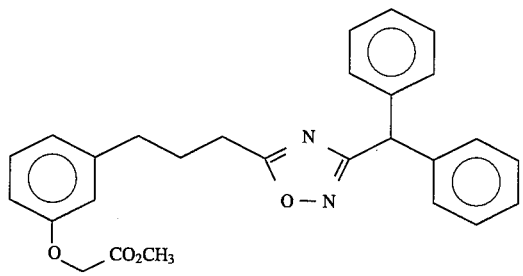

A solution of the compound prepared in reference example 17 (193 mg) in toluene (8 ml) was refluxed overnight. The mixture was evaporated. The residue was purified by flash silica gel chromatography (n-hexane:ethyl acetate= 4:1) to give the title compound (108 mg) having the following physical data.

Example 21

3-[3-(3-diphenylmethyl-1,2,4-oxadiazol-5-yl) propyl]phenoxyacetic acid

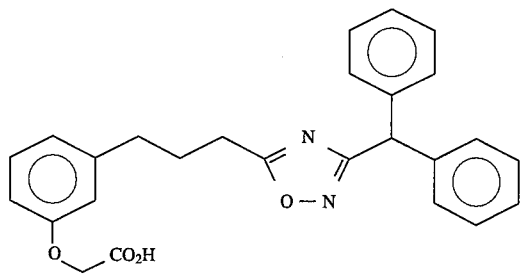

By the same procedure as in example 2, using the compound prepared in example 20 (108 mg), the title compound (102 mg) having the following physical data was given.

TLC: Rf 0.16 (chloroform:methanol=9:1); NMR: δ7.40-7.10 (11H, m), 6.90-6.70 (3H, m), 5.59 (1H, s), 4.62 (2H, s), 2.87 (2H, t, J=7Hz), 2.68 (2H, t, J=7Hz), 2.12 (2H, m).

Example 22

Methyl 3-[3-(5-diphenylmethyl-1,2,4-oxadiazol-3-yl)propyl]phenoxy acetate

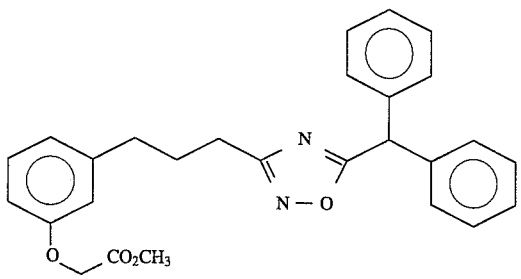

A solution of the compound prepared in reference example 20 (61 mg) in toluene (8.0 ml) was refluxed overnight. The mixture was evaporated. The residue was purified by flash silica gel chromatography (n-hexane:ethyl acetate=4:1) to give the title compound (31 mg) having the following physical data.

NMR: δ7.40–7.10 (11H, m), 6.82 (1H, d, J=7Hz), 6.78 (1H, s), 6.74 (1H, d, J=7Hz), 5.70 (1H, s), 4.60 (2H, s), 3.80 (3H, s), 2.76 (2H, t, J=7Hz), 2.67 (2H, t, J=7Hz), 2.08 (2H, m); MS (m/z): 442 (M+), 251, 167.

Example 23

3-[3-(5-diphenylmethyl-1,2,4-oxadiazol-3-yl)propyl]phenoxyacetic acid

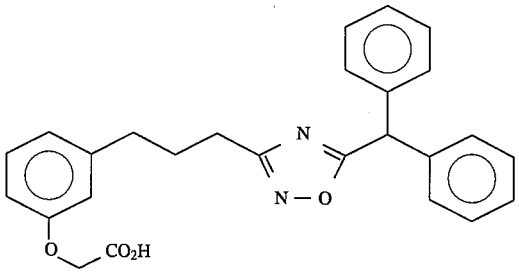

By the same procedure as in example 2, using the compound prepared in example 22 (31 mg), the title compound (30 mg) having the following physical data was given.

TLC: Rf 0.18 (chloroform:methanol=9:1); NMR: δ7.40–7.10 (11H, m), 6.84(1H, d, J=7Hz), 6.77(1H, s), 6.74 (1H, d, J=7Hz), 5.72 (1H, s), 4.63 (2H, s), 2.74 (2H, t, J=7Hz), 2.67 (2H, t, J=7Hz), 2.08 (2H, m).

Formulation Example 1

The following components were admixed in a conventional method and punched out to obtain 100 tablets each containing 5 mg of active ingredient.

| | |
|---|---|
| 3-(4-Diphenylmethyloxyiminobutyl)phenoxy acetic acid | 500 mg |
| Carboxymethylcellulose calcium | 200 mg |
| Magnesium stearate | 100 mg |
| Microcrystalline cellulose | 9.2 g |

Formulation Example 2

The following components were admixed in a conventional manner. The solution was sterilized in conventional manner, 5 ml portions were placed into 10 ml ampoules and freeze-dried to obtain 100 ampoules each containing 2 mg of the active ingredient.

| | |
|---|---|
| 3-(4-Diphenylmethyloxyiminobutyl)phenoxy acetic acid | 200 mg |
| Citric acid, anhydrous | 20 mg |
| Distilled water | 500 ml |

"While the invention has been described in detail and with reference to specific examples thereof, it will be apparent to one skilled in the art that various changes and modifications can be made therein without departing from the spirit and scope thereof."

What is claimed is:

1. A phenoxyacetic acid compound of the formula (I):

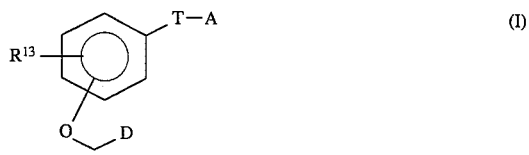

wherein A is i)

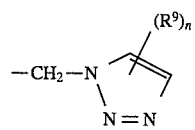

or
ii)

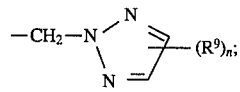

T is i) a single bond; ii) a $C_{1-6}$ alkylene group; iii) a $C_{2-6}$ alkenylene group; or iv) —O—$(CH_2)_s$—;

D is i) —$CO_2R^{10}$ or ii) —$CONR^{11}R^{12}$;

$R^9$ is i) a hydrogen atom; ii) a phenyl group; iii) a $C_{1-4}$ alkyl group; or iv) a $C_{1-4}$ alkyl group substituted by one or two of a phenyl group or a 4–7 membered monocyclic hetero ring containing one nitrogen atom;

$R^{10}$ is a hydrogen atom or a $C_{1-12}$ alkyl group;

$R^{11}$ and $R^{12}$ each, independently, is a hydrogen atom or a $C_{1-4}$ alkyl group, or $R^{11}$ and $R^{12}$ taken together with the nitrogen atom bonded to $R^{11}$ and $R^{12}$ is the residue of an amino acid;

$R^{13}$ is a hydrogen atom, a $C_{1-4}$ alkyl group a $C_{1-4}$ alkoxy group or a nitro group;

s is 2–4;

n is 1–2, provided that when n is 1, $R^9$ is a $C_{1-4}$ alkyl group substituted by one or two of a phenyl group or a 4–7 membered monocyclic hetero ring containing one nitrogen atom, or provided that when n is 2 at least one $R^9$ is a $C_{1-4}$ alkyl group substituted by one or two of a phenyl group or a 4–7 membered monocyclic hetero ring containing one nitrogen atom, and the rings in $R^9$ may be substituted by one to three of a $C_{1-4}$ alkyl group, a $C_{1-4}$ alkoxy group, a halogen atom, a nitro group or a trihalomethyl group;

or a non-toxic salt thereof or a non-toxic acid addition salt thereof.

2. A compound according to claim 1, wherein D is a carboxy group.

3. A compound according to claim 1, wherein D is a $C_{1-12}$ alkoxycarbonyl group.

4. A pharmaceutical composition which comprises, as active ingredient, an effective amount of a phenoxyacetic acid compound of the formula (I) depicted in claim 1 or a non-toxic salt thereof, or a non-toxic acid addtion salt thereof, with a pharmaceutical carrier or coating.

5. A method for the the treatment of thrombosis, arteriosclerosis, ischemic heart diseases, gastric ulcer or hypertension, which comprises administering an effective amount of a phenoxyacetic acid compound of the formula (I) depicted in claim 1 or a non-toxic salt thereof, or a non-toxic acid addtion salt thereof.

6. The compound according to claim 1, wherein A is i)

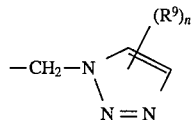

in which $R^9$ and n have the same meaning as defined in claim 1.

7. The compound according to claim 6, which is 3-[3-(4-diphenylmethyl-1,2,3-triazol-1-yl)propyl]phenoxyacetic acid, 3-[3-(4-diphenylmethyl-1,2,3-triazol-3-yl)propyl]phenoxyacetic acid or its methyl ester, or its octyl ester, or its acetamide, or its amide with glycine.

8. The compound according to claim 1, wherein A is ii)

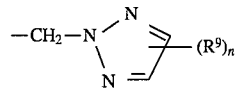

in which $R^9$ and n have the same meaning as defined in claim 1.

9. The compound according to claim 8, which is 3-[3-(4-diphenylmethyl-1,2,3-triazol-2-yl)propyl]phenoxyacetic acid or its methyl ester, or its octyl ester, or its acetamide, or its amide with glycine.

* * * * *